(12) United States Patent
McHardy et al.

(10) Patent No.: US 6,960,609 B2
(45) Date of Patent: Nov. 1, 2005

(54) 1-DIPHENYLMETHYL-PYRAZOLE DERIVATIVES AS OPIOID RECEPTOR LIGANDS

(75) Inventors: Stanton F. McHardy, Coventry, RI (US); Michael G. Vetelino, North Stonington, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 10/201,119

(22) Filed: Jul. 23, 2002

(65) Prior Publication Data

US 2003/0069241 A1 Apr. 10, 2003

Related U.S. Application Data

(60) Provisional application No. 60/307,535, filed on Jul. 24, 2001.

(51) Int. Cl.$^7$ ..................... A61K 31/415; C07D 231/10
(52) U.S. Cl. ..................... 514/406; 548/377.1
(58) Field of Search ........................ 514/406; 548/377.1

(56) References Cited

U.S. PATENT DOCUMENTS 4,118,487 A    10/1978    Regel et al.

FOREIGN PATENT DOCUMENTS

WO        WO0014066        3/2000

OTHER PUBLICATIONS

Fang Wang, et al., "Non–Aqueous Capillary Electrophoresis Chiral Separations with Sulfated Beta–Cyclodextrin", Journal of Chromatography, B: Biiomedical Sciences and Applicaitons (1999). 731(2), pp 187–197, XP004179567 Bifonazole.

Luisa Cerrada, et al., "Azolyl Substituted 1,2 Troeger's Bases", Journal of the Chemical Society, Chemical Communications (1993), (23), pp 1713–1714, XP002219017.

Inayat A. Bhatti, et al., "Pyrolysis of 1–Substituted Pyrazoles and Chloroform at 550 Degree C: Formation of Alpha–Carboline from 1–Benzylpyrazoles", Journal of the Chemical Society, Perkin Transactions 1: Organic and Bio–Organic Chemistry (1997), (24), pp 3581–3585, XP002219018.

Database WPI, Section Ch. Week 198213, Derwent Publications Ltd., London, GB; Class B03, AN 1982-25801E, XP002219019 and SU 883 964 A (Unov Rost), May 30, 1981.

*Primary Examiner*—Kamal Saeed
(74) *Attorney, Agent, or Firm*—Scully, Scott, Murphy & Presser

(57) ABSTRACT

This invention relates to 1-diphenylmethyl-pyrazole derivatives of formula (I):

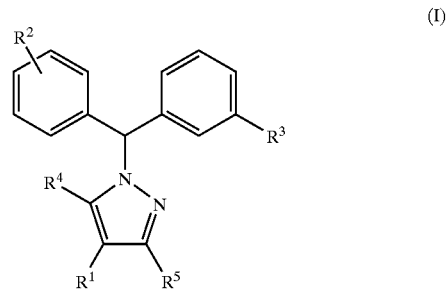

(I)

and pharmaceutically acceptable salts thereof; wherein $R^1$, $R^2$, $R^3$, $R^4$ and $R^5$ are defined herein, as ligands for opioid receptors, particularly the delta opioid receptor. The compounds of the invention have a broad range of therapeutic uses in the area of addictions, analgesia, immunotherapy, shock and brain injuries, neurological dysfunction, gastrointestinal dysfunction, among others.

6 Claims, No Drawings

1-DIPHENYLMETHYL-PYRAZOLE DERIVATIVES AS OPIOID RECEPTOR LIGANDS

This application claims the benefit of U.S. Provisional Application Ser. No. 60/307,535, filed Jul. 24, 2001.

This invention relates to 1-diphenylmethyl-pyrazole derivatives of formula (I):

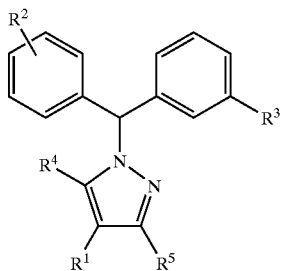

and pharmaceutically acceptable salts thereof; wherein $R^1$, $R^2$, $R^3$, $R^4$ and $R^5$ are defined herein, as ligands for opioid receptors, particularly the delta opioid receptor. The compounds of the invention have a broad range of therapeutic uses in the area of addictions, analgesia, immunotherapy, shock and brain injuries, neurological dysfunction, gastrointestinal dysfunction, among others.

Significant research has focused on understanding the mechanism of action of identified endogenous and non-endogenous opioid compounds, particularly as in the context of cellular and differentiated tissue opioid receptors. Opioid compounds are typically classified by their binding selectivity with respect of these cellular and differentiated tissue receptors to which a specific drug species binds as a ligand. These receptors include the three subtypes of opioid receptors, mu ($\mu$), delta ($\delta$) and kappa ($\kappa$) receptors, which are described and documented in the scientific literature. All three receptors are present in the central and peripheral nervous systems of many species, including man. Activation of delta receptors produces antinociception in rodents and can induce analgesia in man, in addition to influencing motility of the gastrointestinal tract. (see, T. F. Burks in *The Pharmacology Of Opioid Peptides*, Ed. L. F. Tseng (Harwood Academic Publishers 1995)).

The well-known narcotic opioid compounds, such as morphine and its analogs, are selective for the opioid mu receptor. Mu receptors mediate analgesia, respiratory depression, and inhibition of gastrointestinal transit. Kappa receptors mediate analgesia and sedation.

The existence of the opioid delta receptor is a relatively recent discovery which followed the isolation and characterization of endogenous enkephalin peptides, which are ligands for the delta receptor. Research in the past decade has produced significant information about the delta receptor, but a clear picture of its function has not yet emerged. Delta receptors mediate analgesia, but do not appear to inhibit intestinal transit in the manner characteristic of mu receptors.

U.S. Pat. No. 4,816,586, which issued on Mar. 28, 1989 to P. S. Portoghese, refers to various delta opioid receptor antagonists. These compounds are described as possessing a unique opioid receptor antagonist profile, and include compounds that are highly selective for the delta opioid receptor.

U.S. Pat. No. 4,518,711, which issued May 21, 1985 to V. J. Hruby et al., describes cyclic, conformationally constrained analogs of enkephalins. These compounds include both agonists and antagonists for the delta receptor, and are said to induce pharmacological and therapeutic effects, such as analgesia in the case of agonist species of such compounds. The antagonist species of the disclosed compounds are suggested to be useful in the treatment of schizophrenia, Alzheimer's disease, and respiratory and cardiovascular functions.

S. Goenechea, et al., in "Investigation of the Biotransformation of Meclozine in the Human Body," *J. Clin. Chem. Clin. Biochem.*, 1988, 26(2), 105–15, describe the oral administration of a polyaryl piperazine compound in a study of meclozine metabolization in human subjects.

In "Plasma Levels, Biotransformation and Excretion of Oxatomide in Rats, Dogs, and Man," *Xenobiotica*, 1984, 15(6), 445–62, Meuldermans, W., et al. refer to a metabolic study of plasma levels, biotransformation, and excretion of oxatomide.

T. Iwamoto, et al., in "Effects of KB-2796, A New Calcium Antagonist, and Other Diphenylpiperazines on [$^3$H] nitrendipine Binding", *Jpn. J. Pharmacol.*, 1988, 48(2), 241–7, describe the effect of a polyaryl piperazine as a calcium antagonist.

K. Natsuka, et al., in "Synthesis and Structure-Activity Relationships of 1-Substituted 4-(1,2-Diphenylethyl) piperazine Derivatives Having Narcotic Agonist and Antagonist Activity," *J. Med. Chem.*, 1987, 30 (10), 1779–1787, refer to racemates and enantiomers of 1-substituted 4-[2-(3-hydroxyphenyl)-1-phenylethyl] piperazine derivatives.

European Patent Application No. 458,160, published on Nov. 27, 1991, refers to certain substituted diphenylmethane derivatives as analgesic and anti-inflammatory agents, including compounds wherein the methylene bridging group (linking the two phenyl moieties) is substituted on the methylene carbon with a piperidinyl or piperazinyl group.

South African Patent Application No. 8604522, which was published on Dec. 12, 1986, refers to certain N-substituted arylalkyl and aryl-alkylene substituted aminoheterocyclic compounds, including piperidine derivatives, as cardiovascular, antihistamine, and anti-secretory agents.

European Patent Application No. 133,323, published on Feb. 20, 1985, refers to certain diphenylmethyl piperazine compounds as non-sedative antihistamines.

International Patent Publication WO 00/39091, published Jul. 6, 2000 refers to 3,3-biarylpiperidine and 2,2-biarylmorpholine derivatives having the ability to bind to opioid receptors. International Patent Publication WO 00/14066, published Mar. 16, 2000 refers to 4,4-biarylpiperidine derivatives having the ability to bind to opioid receptors. European Patent Application No. 1 038 872, published on Sep. 27, 2000, refers to 4-phenyl-4-heteroarylpiperidine derivatives as opioid receptors.

There is a continuing need in the art for improved opioid compounds, particularly compounds which are free of addictive character and other adverse side effects of conventional opioid compounds, such as morphine and pethidine.

SUMMARY OF THE INVENTION

This invention relates to compounds of the formula (I)

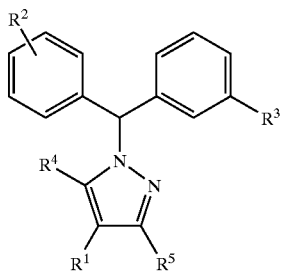

(I)

and pharmaceutically acceptable salts thereof;

wherein $R^1$ is hydrogen, halogen, $(C_1-C_8)$alkyl, $(C_1-C_8)$alkoxy, $(C_1-C_7)$alkoxy-$(C_1-C_7)$alkyl-wherein the total number of carbon atoms is eight or less, aryl, heteroaryl, aryl-$(CH)_m$—, heteroaryl-$(CH)_m$—, $(C_3-C_7)$cycloalkyl-$(CH_2)_m$—, or heterocyclic-$(CH)_m$—, wherein m is an integer between 1 and 8, wherein any of the above aryl moieties is selected, independently, from phenyl and naphthyl, wherein any of the above heteroaryl moieties is selected, independently, from pyrazinyl, benzofuranyl, quinolyl, isoquinolyl, benzothienyl, isobenzofuryl, pyrazolyl, indolyl, isoindolyl, benzimidazolyl, purinyl, carbazolyl, 1,2,5-thiadiazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, oxazolyl, oxadiazolyl, isoxazolyl, thiazolyl, isothiazolyl, furanyl, pyranyl, pyrazolyl, pyrrolyl, tetrazolyl, triazolyl, thienyl, imidazolyl, pyridinyl, pyrimidinyl, thianthrenyl, chromenyl, phenoxathiinyl, indolizinyl, indazolyl, quinolizinyl and naphthyridinyl;

and wherein said heterocyclic moiety is selected from saturated or unsaturated non-aromatic monocyclic or bicyclic ring systems, wherein said monocyclic ring systems contain from four to seven ring carbon atoms, from one to three of which may optionally be replaced with O, N or S, and wherein said bicyclic ring systems contain from seven to twelve carbon atoms, from one to four of which may optionally be replaced with O, N or S; and wherein any of the above aryl, heteroaryl or heterocyclic moieties of $R^1$ may optionally be substituted with from one to three substituents, preferably with one or two substituents, independently selected from halogen (i.e., chloro, fluoro, bromo or iodo), $(C_1-C_6)$alkyl optionally substituted with from one to seven (preferably with from zero to four) fluorine atoms, phenyl, benzyl, hydroxy, acetyl, formyl, amino, cyano, nitro, $(C_1-C_6)$alkoxy, $(C_1-C_6)$alkylamino, $[(C_1-C_6)alkyl]_2$amino, benzylamino$(C_1-C_8)$alkyl, $(C_1-C_8)$alkylamino$(C_1-C_8)$alkyl, $(R^6)_2$amino$(C_1-C_8)$alkyl wherein each $R^6$ is $(C_1-C_6)$alkyl or two $R^6$ groups join to form a saturated 4 to 6-membered ring optionally containing one heteroatom selected from O, N or S, said 4 to 6-membered ring optionally substituted by a $(C_1-C_6)$alkyl or a benzo group at any two adjacent carbon atoms, and wherein any of alkyl moieties in $R^1$ (e.g., the alkyl moieties of alkyl, alkoxy or alkylamino groups) may optionally be substituted with from one to seven (preferably with from zero to four) fluorine atoms;

$R^2$ is hydrogen, halogen (i.e., chloro, fluoro, bromo or iodo), aryl, heteroaryl, heterocyclic, $SO_2R^7$, $COR^7$, $CONR^8R^9$, $COOR^7$, or $C(OH)R^8R^9$ wherein each of $R^7$, $R^8$ and $R^9$ is defined, independently, as $R^1$ is defined above, or $R^7$ and $R^8$, together with the carbon or nitrogen to which they are both attached, form a three to seven membered saturated ring containing from zero to three heteroatoms selected, independently, from O, N and S, and wherein said aryl, heteroaryl, and heterocyclic are defined as such terms are defined above in the definition of $R^1$, and wherein any of the aryl, heteroaryl and heterocyclic moieties of $R^2$ may optionally be substituted with from one to three substituents, preferably with one or two substituents, independently selected from halo (i.e., chloro, fluoro, bromo or iodo), $(C_1-C_6)$alkyl optionally substituted with from one to seven (preferably with from zero to four) fluorine atoms, phenyl, benzyl, hydroxy, acetyl, amino, cyano, nitro, $(C_1-C_6)$alkoxy optionally substituted with from one to seven (preferably with from zero to four) fluorine atoms, $(C_1-C_6)$alkylamino and $[(C_1-C_6)alkyl]_2$amino;

$R^3$ is hydrogen, hydroxy, —$(C_1-C_6)$alkyl-OH, $(C_1-C_6)$alkoxy, —$(C_1-C_7)$alkyl-$(C_1-C_7)$alkoxy, $NHSO_2R^7$, $C(OH)R^7R^8$, fluorine, bromine, chlorine, iodine, triazolyl, tetrazolyl, heteroaryl, as defined for $R^1$ above or $CONHR^7$, wherein $R^7$ and $R^8$ are the same or different and are selected from hydrogen, $(C_1-C_4)$alkyl, $(C_1-C_4)$alkoxy and $(C_1-C_4)$alkoxy-$(C_1-C_4)$alkyl having a total of 4 or less carbon atoms, and wherein any of the alkyl moieties of $R^7$ and $R^8$ may optionally be substituted with from one to seven (preferably with from zero to four) fluorine atoms;

$R^4$ and $R^5$ are each, independently, hydrogen, $(C_1-C_8)$alkyl, $(C_1-C_8)$branched alkyl, $(C_3-C_7)$cycloalkyl-, or $(C_3-C_7)$cycloalkyl-$(C_1-C_8)$alkyl.

Preferred embodiments of the present invention are directed to compounds of the formula (I) and pharmaceutically acceptable salts thereof;

wherein $R^1$ is hydrogen, halogen, $(C_1-C_8)$alkyl, $(C_1-C_8)$alkoxy, $(C_1-C_7)$alkoxy-$(C_1-C_7)$alkyl-wherein the total number of carbon atoms is eight or less, aryl, heteroaryl, $(C_3-C_7)$cycloalkyl-, heterocyclic, aryl-$(CH)_m$—, heteroaryl-$(CH)_m$—, $(C_3-C_7)$cycloalkyl-$(CH)_m$—, or heterocyclic-$(CH)_m$—, wherein m is an integer between 1 and 8, wherein the aryl and heteroaryl moieties are as defined previously; and wherein said heterocyclic moiety is selected from saturated or unsaturated non-aromatic monocyclic or bicyclic ring systems, wherein said monocyclic ring systems contain from four to seven ring carbon atoms, from one to two of which may optionally be replaced with O, N or S, and wherein said bicyclic ring systems contain from seven to twelve carbon atoms, from one to two of which may optionally be replaced with O, N or S; and wherein the aryl, heteroaryl or heterocyclic moieties in $R^1$ may optionally be substituted with from one to three substituents, preferably with one or two substituents, independently selected from halogen (i.e., chloro, fluoro, bromo or iodo), $(C_1-C_6)$alkyl optionally substituted with from one to seven (preferably with from zero to four) fluorine atoms, phenyl, benzyl, hydroxy, acetyl, formyl, amino, cyano, nitro, $(C_1-C_6)$alkoxy, $(C_1-C_6)$ alkylamino, $[(C_1-C_6)alkyl]_2$amino, benzylamino $(C_1-C_8)$alkyl, $(C_1-C_8)$alkylamino$(C_1-C_8)$alkyl, $(R^6)_2$ amino$(C_1-C_8)$alkyl wherein each $R^6$ is $(C_1-C_6)$alkyl or two $R^5$ groups join to form a saturated 4 to 6-membered ring optionally containing one heteroatom selected from O, N or S, said 4 to 6-membered ring optionally substituted by a $(C_1-C_6)$alkyl or a benzo group at any two adjacent carbon atoms, and wherein any of alkyl moieties in $R^1$ (e.g., the alkyl moieties of alkyl, alkoxy or alkylamino groups) may optionally be substituted with from one to seven (preferably with from zero to four) fluorine atoms;

$R^2$ is hydrogen, aryl, halo (i.e., chloro, fluoro, bromo or iodo), heteroaryl, heterocyclic, $SO_2R^7$, $COR^7$, $CONR^8R^9$, $COOR^7$, or $C(OH)R^8R^9$ wherein each of $R^7$, $R^8$ and $R^9$ is defined, independently, as $R^1$ is defined above, or $R^7$ and $R^8$, together with the carbon or nitrogen to which they are both attached, form a three to seven membered saturated ring containing from zero to three heteroatoms selected, independently, from O, N and S, and wherein said aryl, heteroaryl, and heterocyclic are defined as such terms are defined above in the definition of $R^1$, and wherein any of the aryl, heteroaryl and heterocyclic moieties of $R^2$ may optionally be substituted with from one to three substituents, preferably with one or two substituents, independently selected from halo (i.e., chloro, fluoro, bromo or iodo), $(C_1-C_6)$alkyl optionally substituted with from one to seven (preferably with from zero to four) fluorine atoms, phenyl, benzyl, hydroxy, acetyl, amino, cyano, nitro, $(C_1-C_6)$alkoxy optionally substituted with from one to seven (preferably with from zero to four) fluorine atoms, $(C_1-C_6)$alkylamino and $[(C_1-C_6)alkyl]_2$amino;

$R^3$ is hydrogen, hydroxy, —$(C_1-C_6)$alkyl-OH, $(C_1-C_6)$ alkoxy, —$(C_1-C_6)$alkyl-$(C_1-C_8)$alkoxy, $NHSO_2R^7$, $C(OH)R^7R^8$, fluorine, bromine, chlorine, iodine, triazolyl, tetrazolyl, heteroaryl, as defined for $R^1$ above or $CONHR^7$, wherein $R^7$ and $R^8$ are the same or different and are selected from hydrogen, $(C_1-C_4)$alkyl, $(C_1-C_4)$alkoxy and $(C_1-C_4)$alkoxy-$(C_1-C_4)$alkyl having a total of 4 or less carbon atoms, and wherein any of the alkyl moieties of $R^7$ and $R^8$ may optionally be substituted with from one to seven (preferably with from zero to four) fluorine atoms;

$R^4$ and $R^5$ are each, independently, hydrogen, $(C_1-C_8)$ alkyl, $(C_1-C_8)$branched alkyl, $(C_3-C_7)$cycloalkyl- or $(C_3-C_7)$cycloalkyl-$(C_1-C_8)$alkyl.

More preferred embodiments of the invention are compounds of the formula (I) and pharmaceutically acceptable salts thereof;

wherein $R^1$ is hydrogen, halogen, $(C_1-C_8)$alkyl, naphthyl, phenyl, or heterocyclic selected from the group consisting of thienyl, thianthrenyl, furanyl, pyranyl, benzofuranyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, and cinnolinyl;

wherein the above phenyl, naphthyl or heterocyclic groups may optionally be substituted with one or two substituents, independently selected from halogen (i.e., chloro, fluoro, bromo or iodo), hydroxy, $(C_1-C_6)$alkyl optionally substituted with from one to seven (preferably with from zero to four) fluorine atoms, formyl, $(C_1-C_8)$alkylamino$(C_1-C_8)$alkyl, and $(R^6)_2$ amino$(C_1-C_8)$alkyl wherein each $R^6$ is $(C_1-C_6)$alkyl or two $R^6$ groups join to form a saturated 4 to 6-membered ring optionally containing one heteroatom selected from O, N or S, said 4 to 6-membered ring optionally substituted by a $(C_1-C_6)$alkyl or a benzo group at any two adjacent carbon atoms; and $R^2$ is $CONR^8R^9$ or $COOR^7$, wherein each of $R^7$, $R^8$ and $R^9$ is $(C_1-C_6)$alkyl optionally substituted with from one to seven (preferably with from zero to four) fluorine atoms;

$R^3$ is hydroxy, $(C_1-C_8)$alkoxy, or halogen; and $R^4$ and $R^5$ are independently is hydrogen or $(C_1-C_8)$alkyl.

The most preferred embodiments of the present invention are compounds of formula (I) and pharmaceutically acceptable salts thereof;

wherein $R^1$ is H, halogen, furanyl, thienyl, naphthyl or phenyl, wherein the furanyl, thienyl, naphthyl or phenyl group may optionally be substituted with one or more halogen, hydroxy, trifluoromethyl, alkyl, formyl, $(C_1-C_6)$alkylaminomethyl, $((C_1-C_6))_2$aminomethyl, piperidinylmethyl, azetidinylmethyl, $(C_1-C_6)$ alkylpipiridinylmethyl, benzylaminomethyl, morpholinylmethyl, thiomorpholinylmethyl, isoquinolinylmethyl, or quinolinylmethyl;

$R^2$ is $(C_1-C_6)$alkylaminocarbonyl, $((C_1-C_6))_2$aminocarbonyl or alkoxycarbonyl;

$R^3$ is hydroxy or $(C_1-C_6)$alkoxy; and $R^4$ and $R^5$ are independently either H or $(C_1-C_6)$alkyl.

Specific embodiments of the invention are set forth in the Examples in this description. More preferred specific embodiments of the invention are the following:

N,N-Diethyl-4-[[4-(4-fluoro-phenyl)-3,5-dimethyl-pyrazol-1-yl]-(3-hydroxy-phenyl)-methyl]-benzamide;

4-[(3,5-Dimethyl-pyrazol-1-yl)-(3-hydroxy-phenyl)-methyl]-N,N-diethyl-benzamide;

4-[(4-Bromo-3,5-dimethyl-pyrazol-1-yl)-(3-hydroxy-phenyl)-methyl]-N,N-diethyl-benzamide;

N,N-Diethyl-4-[(3-hydroxy-phenyl)-(4-iodo-3,5-dimethyl-pyrazol-1-yl)-methyl]-benzamide;

4-[(3,5-Dimethyl-4-phenyl-pyrazol-1-yl)-(3-hydroxy-phenyl)-methyl]-N,N-diethyl-benzamide;

4-[[4-(4-Chloro-phenyl)-3,5-dimethyl-pyrazol-1-yl]-(3-hydroxy-phenyl)-methyl]-N,N-diethyl-benzamide;

4-[(3,5-Dimethyl-4-p-tolyl-pyrazol-1-yl)-(3-hydroxy-phenyl)-methyl]-N,N-diethyl-benzamide;

4-[[3,5-Dimethyl-4-(4-trifluoromethyl-phenyl)-pyrazol-1-yl]-(3-hydroxy-phenyl)-methyl]-N,N-diethyl-benzamide;

4-[(3,5-Dimethyl-4-m-tolyl-pyrazol-1-yl)-(3-hydroxy-phenyl)-methyl]-N,N-diethyl-benzamide;

4-[(3,5-Dimethyl-4-o-tolyl-pyrazol-1-yl)-(3-hydroxy-phenyl)-methyl]-N,N-diethyl-benzamide;

4-[[4-(3,5-Dichloro-phenyl)-3,5-dimethyl-pyrazol-1-yl]-(3-hydroxy-phenyl)-methyl]-N,N-diethyl-benzamide;

4-[[4-(2,4-Dichloro-phenyl)-3,5-dimethyl-pyrazol-1-yl]-(3-hydroxy-phenyl)-methyl]-N,N-diethyl-benzamide;

N,N-Diethyl-4-[(4-furan-2-yl-3,5-dimethyl-pyrazol-1-yl)-(3-hydroxy-phenyl)-methyl]-benzamide;

4-[(3,5-Dimethyl-4-thiophen-2-yl-pyrazol-1-yl)-(3-hydroxy-phenyl)-methyl]-N,N-diethyl-benzamide;

4-[(3,5-Dimethyl-4-thiophen-3-yl-pyrazol-1-yl)-(3-hydroxy-phenyl)-methyl]-N,N-diethyl-benzamide;

4-[(3,5-Dimethyl-4-naphthalen-1-yl-pyrazol-1-yl)-(3-hydroxy-phenyl)-methyl]-N,N-diethyl-benzamide;

4-[(3,5-Dimethyl-pyrazol-1-yl)-(3-hydroxy-phenyl)-methyl]-N,N-dipropyl-benzamide;

Azepan-1-yl-{4-[(3,5-dimethyl-pyrazol-1-yl)-(3-hydroxy-phenyl)-methyl]-phenyl}-methanone;

N,N-Dibutyl-4-[(3,5-dimethyl-pyrazol-1-yl)-(3-hydroxy-phenyl)-methyl]-benzamide;

4-[(3,5-Dimethyl-pyrazol-1-yl)-(3-hydroxy-phenyl)-methyl]-N,N-diisopropyl-benzamide;

4-[[3,5-Dimethyl-4-(2-piperidin-1-ylmethyl-phenyl)-pyrazol-1-yl]-(3-hydroxy-phenyl)-methyl]-N,N-diethyl-benzamide;

4-[[4-(2-Diethylaminomethyl-phenyl)-3,5-dimethyl-pyrazol-1-yl]-(3-hydroxy-phenyl)-methyl]-N,N-diethyl-benzamide;

4-[[4-(2-Azetidin-1-ylmethyl-phenyl)-3,5-dimethyl-pyrazol-1-yl]-(3-hydroxy-phenyl)-methyl]-N,N-diethyl-benzamide;

4-[[3,5-Dimethyl-4-(2-morpholin-4-ylmethyl-phenyl)-pyrazol-1-yl]-(3-hydroxy-phenyl)-methyl]-N,N-diethyl-benzamide;

4-[(3,5-Dimethyl-pyrazol-1-yl)-phenyl-methyl]-N,N-diethyl-benzamide

4-[(3,5-Dimethyl-pyrazol-1-yl)-(3-fluoro-phenyl)-methyl]-N,N-diethyl-benzamide (−)-4-[(3,5-Dimethyl-pyrazol-1-yl)-(3-hydroxy-phenyl)-methyl]-N,N-diethyl-benzamide (+)-4-[(3,5-Dimethyl-pyrazol-1-yl)-(3-hydroxy-phenyl)-methyl]-N,N-diethyl-benzamide and pharmaceutically acceptable salts thereof.

The present invention also relates to the pharmaceutically acceptable salts of the compounds of formula (I). The pharmaceutically acceptable salts of the invention may be acid addition and base addition salts of compounds of the formula (I). The acids which are used to prepare the pharmaceutically acceptable acid addition salts of the aforementioned base compounds of this invention are preferably those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts. The chemical bases that are used as reagents to prepare the pharmaceutically acceptable base salts of this invention are those which form non-toxic base salts with the acidic compounds of formula (I). Such non-toxic base salts include those derived from such pharmacologically acceptable cations as sodium, potassium, calcium and magnesium, etc.

This invention also relates to a method of treating a disease, disorder or condition, the treatment of which can be effected or facilitated by modulating binding to opioid receptors in a mammal, including a human, comprising administering to a mammal in need of such treatment an amount of a compound of the formula (I), or a pharmaceutically acceptable salt thereof, that is effective in treating such disorder or condition. This invention also relates to a method for treating a disease disorder or condition, the treatment of which can be effected or facilitated by modulating binding to opioid receptors in a mammal, including a human, comprising administering to a mammal in need of such treatment an opioid receptor binding modulating effective amount of a compound of the formula (I) or a pharmaceutically acceptable salt thereof.

This invention also relates to a method of treating a condition selected from the group consisting of inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, non-ulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e.g., addictions to or dependencies on alcohol, opioid compounds, benzodiazepines, nicotine, heroin or cocaine), chronic pain, non-somatic pain, acute pain and neurogenic pain, systemic lupus erythematosus, Hodgkin's disease, Sjogren's disease, epilepsy and rejection in organ transplants and skin grafts in a mammal, including a human, comprising administering to a mammal in need of such treatment an amount of a compound of the formula (I) that is effective in treating such condition.

This invention also relates to a method for treating a condition selected from the group consisting of inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, non-ulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e.g., addictions to or dependencies on alcohol, opiates, benzodiazepines, nicotine, heroin or cocaine), chronic pain, non-somatic pain, acute pain and neurogenic pain, systemic lupus erythematosus, Hodgkin's disease, Sjogren's disease, epilepsy and rejection in organ transplants and skin grafts, in a mammal, including a human, comprising administering to the mammal an opioid receptor binding modulating effective amount of a compound of the formula (I), or a pharmaceutically acceptable salt thereof.

This invention also relates to a pharmaceutical composition for treating a disorder or condition, the treatment of which can be effected or facilitated by modulating (i.e., increasing or decreasing) binding to opioid receptors in a mammal, including a human, comprising an amount of a compound of the formula (I), or a pharmaceutically acceptable salt thereof, that is effective in treating such disorder or condition and a pharmaceutically acceptable carrier. This invention also relates to a pharmaceutical composition for treating a disorder or condition, the treatment of which can be effected or facilitated by modulating binding to opioid receptors in a mammal, including a human, comprising an opioid receptor binding modulating effective amount of a compound of the formula (I), or a pharmaceutically acceptable salt thereof, and a pharmaceutically acceptable carrier.

This invention also relates to a pharmaceutical composition for treating a disorder or condition selected from inflammatory diseases such as arthritis (e.g., rheumatoid arthritis and osteoarthritis), psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, non-ulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e.g., addictions to or dependencies on alcohol, opioid compounds, benzodiazepines, nicotine, heroin or cocaine), chronic pain, non-somatic pain, acute pain and neurogenic pain, systemic lupus erythematosus, Hodgkin's disease, Sjogren's disease, epilepsy and rejection in organ transplants and skin grafts in a mammal, including a human, comprising a glutamate neurotransmission modulating effective amount of a compound of the formula (I), or a pharmaceutically salt thereof, and a pharmaceutically acceptable carrier.

This invention also relates to a pharmaceutical composition for treating a condition selected from inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, non-ulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e.g., addictions to or dependencies on alcohol, opioid compounds, benzodiazepines, nicotine, heroin or cocaine), chronic pain, non-somatic pain, acute pain and neurogenic pain, systemic lupus erythematosus, Hodgkin's disease, Sjogren's disease, epilepsy and rejection in organ transplants and skin grafts in a mammal, comprising an amount of a compound of the formula (I) that is effective in treating such condition and a pharmaceutically acceptable carrier.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

The term "alkoxy", as used herein, means "—O-alkyl", wherein "alkyl" is defined as above.

The term "alkylene", as used herein, means an alkyl group having two available binding sites (i.e., -alkyl-, wherein alkyl is defined as above).

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

Compounds of the formula (I) may have chiral centers and therefore may exist in different enantiomeric and diastereomeric forms. This invention relates to all optical isomers and all other stereoisomers (enantiomers, diastereomers, etc.) of compounds of the formula (I), and to all racemic and other mixtures thereof, and to all pharmaceutical compositions and methods of treatment defined above that contain or employ such isomers or mixtures.

Formula (I) above includes compounds identical to those depicted but for the fact that one or more hydrogen or carbon atoms are replaced by isotopes thereof. Such compounds are useful as research and diagnostic tools in metabolism pharmacokinetic studies and in binding assays. Specific applications in research include radioligand binding assays, autoradiography studies and in vivo binding studies.

DETAILED DESCRIPTION OF THE INVENTION

The compounds of formula (I) can be prepared according to the methods illustrated in Schemes 1 through 6 and discussed below. In the reaction schemes and discussion that follow, unless indicated, $R^1$, $R^2$, $R^3$, $R^4$ $R^5$, $R^6$, $R^7$, $R^8$ and $R^9$ and structural formula (I) are defined as above.

Scheme 1 illustrates a method for the preparation of compounds having the basic benzhydrylpyrazole skeleton, in particular, compounds of formula (I) wherein $R^1$, $R^4$ and $R^5$ are as defined above, $R^2$ is $CON((C_1-C_6)alkyl)_2$, and $R^3$ is $(C_1-C_6)$alkoxy. Scheme 2 illustrates means for transforming the $R^3$ group to the full panoply of moieties indicated for that group from the $(C_1-C_6)$alkoxy group of formula (V). Scheme 3 illustrates an alternative means for the preparation of compounds having the basic benzhydrylpyrazole skeleton, compounds of formula (XI), which are compounds of formula (I) wherein $R^1$ and $R^3$ are as defined above, except that they are not halo, and wherein $R^4$ and $R^5$ are as defined above, $R^2$ is $COO(C_1-C_6)$alkyl. Scheme 4 illustrates means for preparing the amide compounds of formula (V) from the carboxylate ester compounds of formula (X). Scheme 5 indicates means by which aminoalkylene substitution may be introduced on the aromatic groups with the $R^1$ group of compounds of formula (V). Scheme 6 illustrates means for transforming the $R^2$ group of compounds of formula (V) to the full panoply of moieties indicated for that group from the amide group at the position in compounds of formula (V).

Referring to Scheme 1, a benzhydryl chloride derivative of formula (II) (wherein Y is $(C_1-C_6)$alkyl) is heated with a pyrazole of formula (III) (wherein X or halo is, e.g., Cl, Br or I) and a tetraalkyl ammonium iodide catalyst, preferably tetra-n-butyl ammonium iodide, in a suitable solvent, preferably acetonitrile, at temperatures ranging from 50° C. to 110° C., preferably at about the reflux temperature of the solvent, to produce a compound of formula (IV). Treatment of a compound of formula (IV) with an appropriately substituted aryl or heteroaryl boronic acid of formula $R^1B(OH)_2$ (where $R^1$ is as defined above) and tetrakis(triphenylphosphine)palladium(0), sodium carbonate in ethanol/water mixture at temperatures ranging from 30° C. to 110° C., preferably at about the reflux temperature, to produce the corresponding compound of formula (V).

Scheme 1

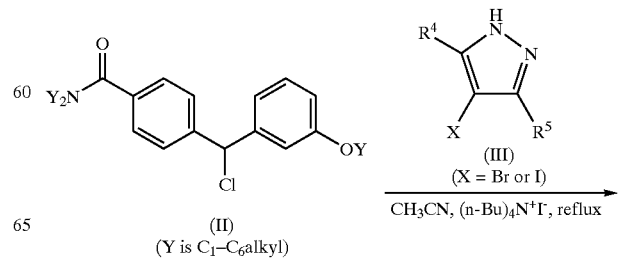

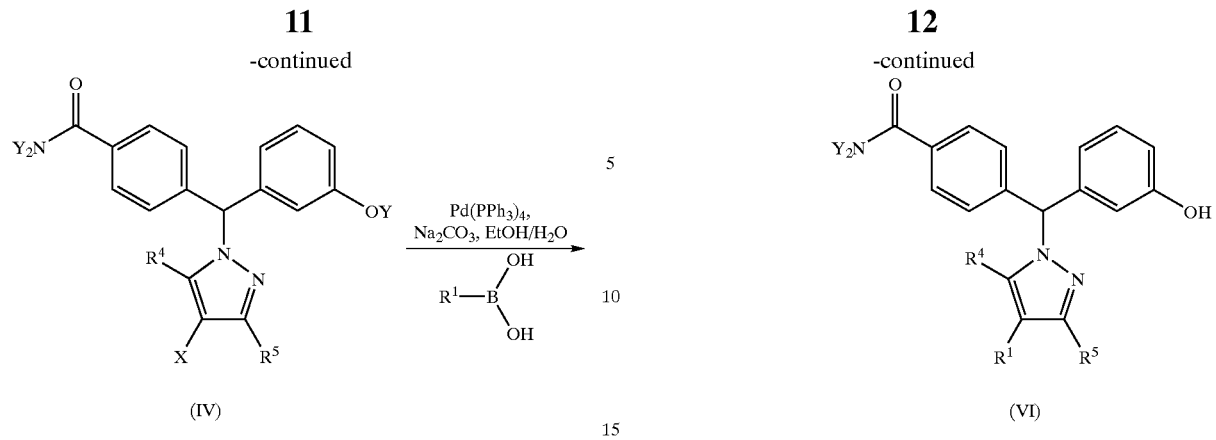

(IV) → (VI)

Referring to Scheme 2, compounds of general formula (I) (where $R^3$ is hydroxy and $R^2$ is a dialkylamide) can be prepared by deprotecting the corresponding alkyl ether of formula (V) (wherein Y is $(C_1-C_6)$alkyl) with aqueous hydrobromic acid and acetic acid, or alternatively, with sodium ethanethiolate in dimethylformamide, at a temperature ranging from about 0° C. to the reflux temperature, to produce the corresponding phenol compounds of formula VI. The reaction is carried out preferably at reflux temperature when hydrobromic acid/acetic acid is used, or at about 100° C. to 120° C. when sodium ethanemethiolate is employed.

Scheme 3 illustrates a method for the preparation of compounds of formula (XI) (or of formula (I) wherein $R^2$ is $COO(C_1-C_6)$alkyl, $R^1$ and $R^3$ are as defined above except $R^3$ is not chloro, bromo or iodo, and $R^4$ and $R^5$ are as defined above. Referring to Scheme 3, a 4-formylbenzoate alkyl ester of formula (VII) is treated with a magnesium grignard reagent generated from a bromide of formula (VIII) in a suitable solvent, preferably tetrahydrofuran or diethyl ether, at temperatures ranging from −78° C. to room temperature, preferably at about room temperature, to produce an intermediate benzhydryl alcohol. The intermediate crude benzhydryl alcohol (not depicted) is then treated with thionyl chloride in a suitable solvent, preferably methylene chloride or dichloroethane, at temperatures ranging from room temperature to solvent reflux temperature, preferably at about reflux temperature, to produce the corresponding benzhydryl chloride of formula (IX). Treatment of a chloride of formula (IX) with pyrazole of formula (X) and a tetra-alkyl ammonium iodide catalyst, preferably tetra-n-butyl ammonium iodide, in a suitable solvent, preferably acetonitrile, at temperatures ranging from 50° C. to 110° C., preferably at about the reflux temperature of the solvent, produces the corresponding product of formula (XI).

Scheme 2

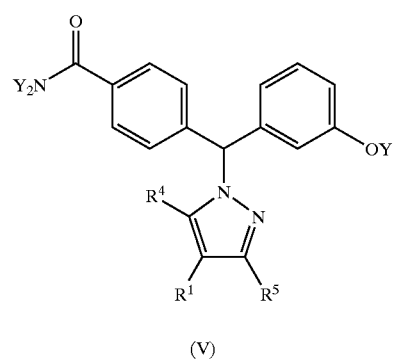

Scheme 3

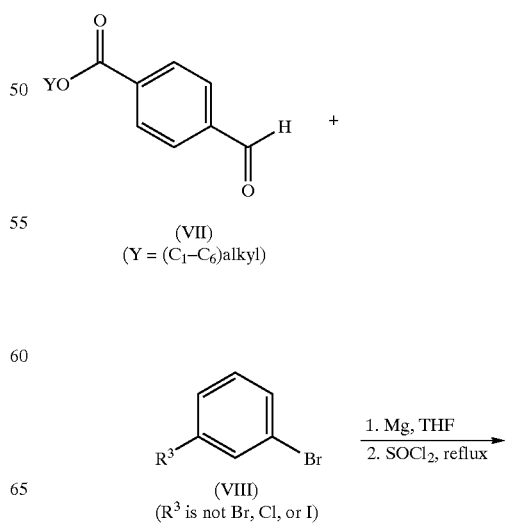

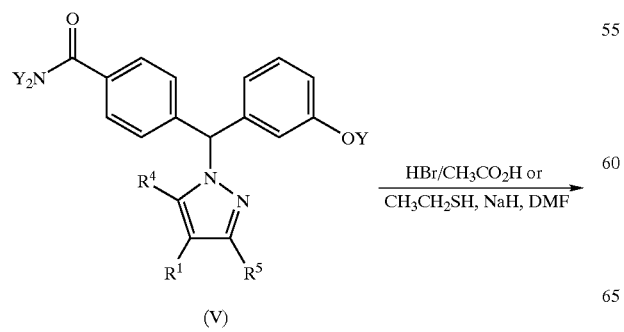

13
-continued

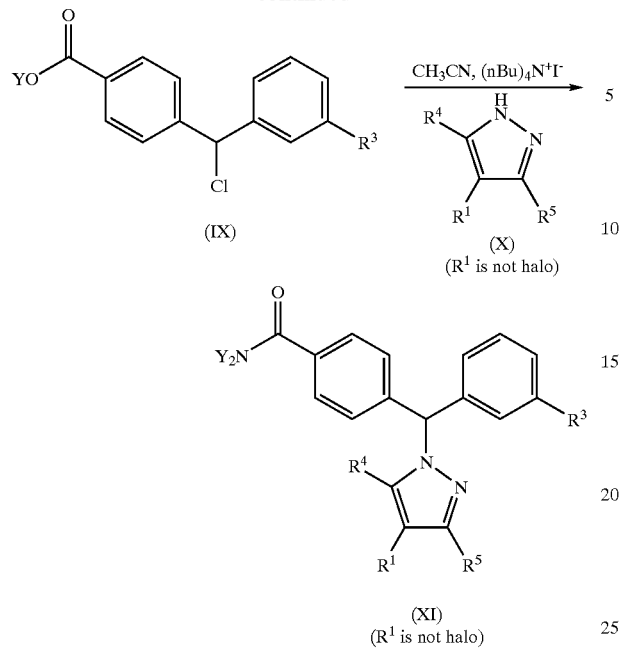

(IX)

(X)
(R¹ is not halo)

(XI)
(R¹ is not halo)

As set forth in Scheme 4, compounds of formula (VI) (or of general formula (I) where $R^2$ is $CONY_2$ where Y is $(C_1-C_6)$alkyl, and $R^3$ is hydroxy) can be prepared by treatment of the ester of formula (XI) with an aluminum amide of a primary or secondary amine, for example, dimethyl amine, in a suitable solvent, preferably dichloroethane or toluene, at a temperature ranging from about 20° C. to about the reflux temperature, preferably at about the reflux temperature of the solvent, which provides the corresponding amide. Deprotecting of the corresponding alkyl ether compound (wherein Y is $(C_1-C_6)$alkyl) with aqueous hydrobromic acid and acetic acid, or with sodium ethanethiolate in dimethylformamide, at a temperature ranging from about 0° C. to the reflux temperature, producing the corresponding phenol compound of formula (VI). When hydrobromic acid/acetic acid is used in this step, reflux temperature is preferred, and when sodium ethanethiolate is used, a preferred temperature range is about 100° C. to 120° C. is preferred. Compounds of formula (VI) may be used to form other compounds of formula (I) with $R^3$ group other than hydroxy via methods as set forth further below in Scheme 6.

Scheme 4

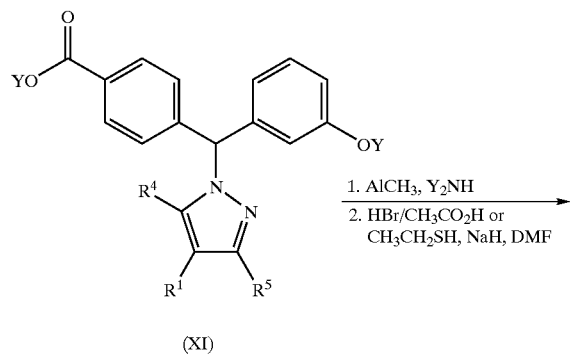

(XI)

1. AlCH₃, Y₂NH
2. HBr/CH₃CO₂H or CH₃CH₂SH, NaH, DMF

14
-continued

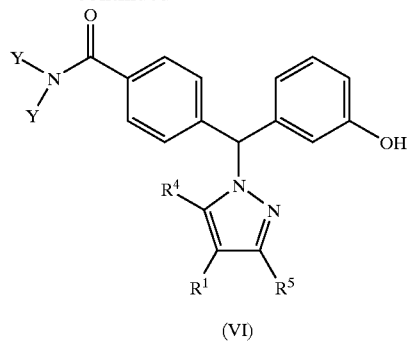

(VI)

As set forth below, scheme 5 illustrates a method for preparing compounds of general formula (I) where $R^3$ is hydroxy, $R^2$ is $CON(Y)_2$ and $R^1$ is a phenyl ring, optionally substituted with $CH_2NR^9R^{10}$. Treatment of the pyrazole of formula (IV) with the appropriately substituted benzaldehyde-boronic acid reagent produces the corresponding coupled product of formula (XII) under conditions analogous to those set forth in Scheme 1. Treatment of the compound of formula (XII) with a suitably substituted amine and a reducing agent (i.e., reductive amination conditions), preferably the amine and sodium triacetoxyborohydride, sodium borohydride or sodium cyanoborohydride, more preferably sodium triacetoxyborohydride, in a suitable solvent, such as dichloromethane, 1,2-dichloroethane, methanol, ethanol or toluene, at a temperature ranging from about 0° C. to 100° C., preferably at about room temperature, yields the desired corresponding benzyl amine derivative. Treatment of this crude product with aqueous hydrobromic acid and acetic acid at temperatures ranging from 25° C. to 120° C., preferably at about the reflux temperature yields the final product of formula (XIII).

Scheme 5

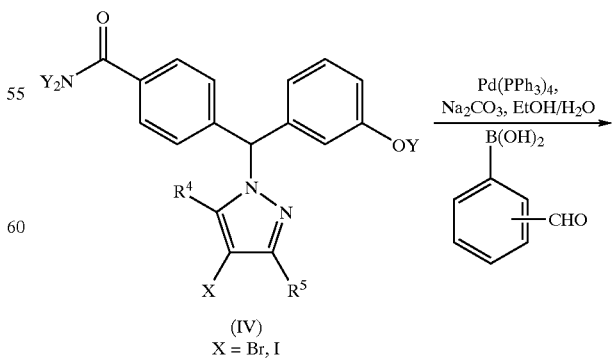

Pd(PPh₃)₄, Na₂CO₃, EtOH/H₂O (IV)
X = Br, I

-continued

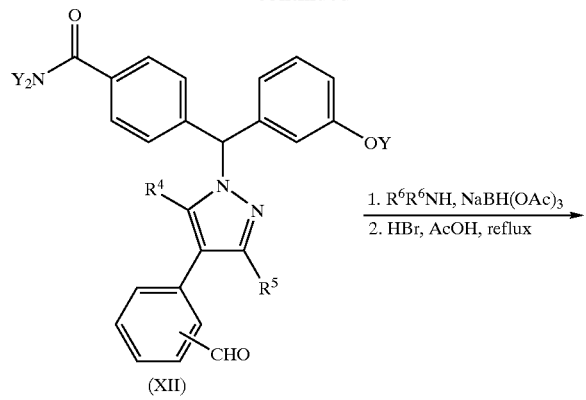

Further illustrated in Schemes 6 through 8 are means for converting phenol compounds of formula (VI) to other compounds of formula (I), i.e., where $R^3$ is defined above. As set forth below in Scheme 6, phenols of general formula (VI) may be treated with trifluoromethanesulfonic anhydride in the presence of a base such as triethylamine to produce the corresponding trifluoromethane sulfonate esters of general formula (XIV) ($R^3$ is OTf). Nitrile compounds of formula (XV) ($R^3$ is CN) may be prepared by treatment of the triflate compounds of formula (XIV) with zinc cyanide in the presence of a suitable catalyst such as tetrakis(triphenylphosphine)palladium in a solvent, such as dimethylformamide, at temperatures ranging from 20° C. to solvent reflux temperature, preferably at about the solvent reflux temperature. Compounds of the general formula (XVI) ($R^3$ is tetrazolyl) can be prepared from the nitrile compounds of formula (XV), via treatment with azidotrimethylsilane in the presence of a dialkyltin oxide (e.g. dibutyltin oxide) in toluene, at temperatures ranging from about 20° C. to about the solvent reflux temperature, preferably at about reflux. Compounds of the general formula (XVII) ($R^3$ is —$CONH_2$) may then be prepared from the nitrile compounds of formula (XV) by treatment with hydrogen peroxide and an alkali metal carbonate (e.g. sodium carbonate) in methanol at temperatures ranging from 0° C. to about room temperature, preferably at about room temperature. The compounds of formula (XVII) may also be modified to alkyl (or alkoxy) aminocarbonyl compounds (i.e., where ($R^3$ is —$CONHR^7$ where $R^7$ is ($C_1$–$C_4$)alkyl, ($C_1$–$C_4$)alkoxy or ($C_1$–$C_4$)alkoxy-($C_1$–$C_4$)alkyl) via routine alkylation reactions.

Scheme 6

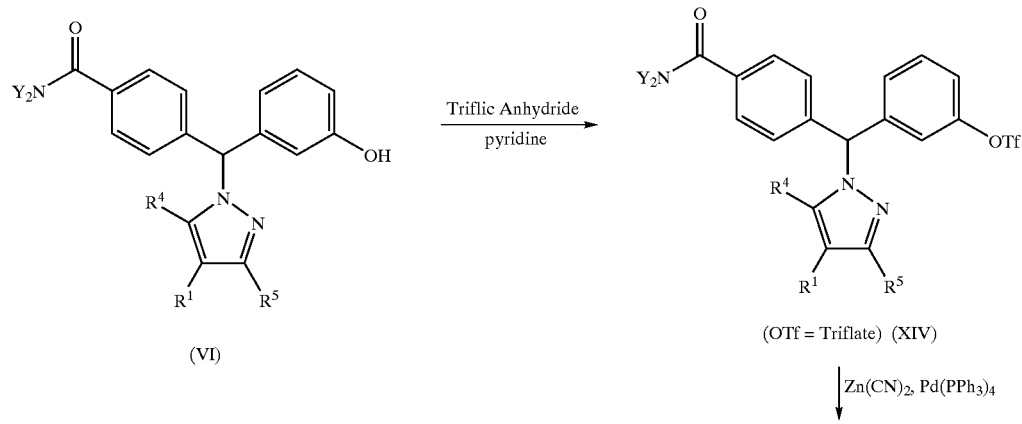

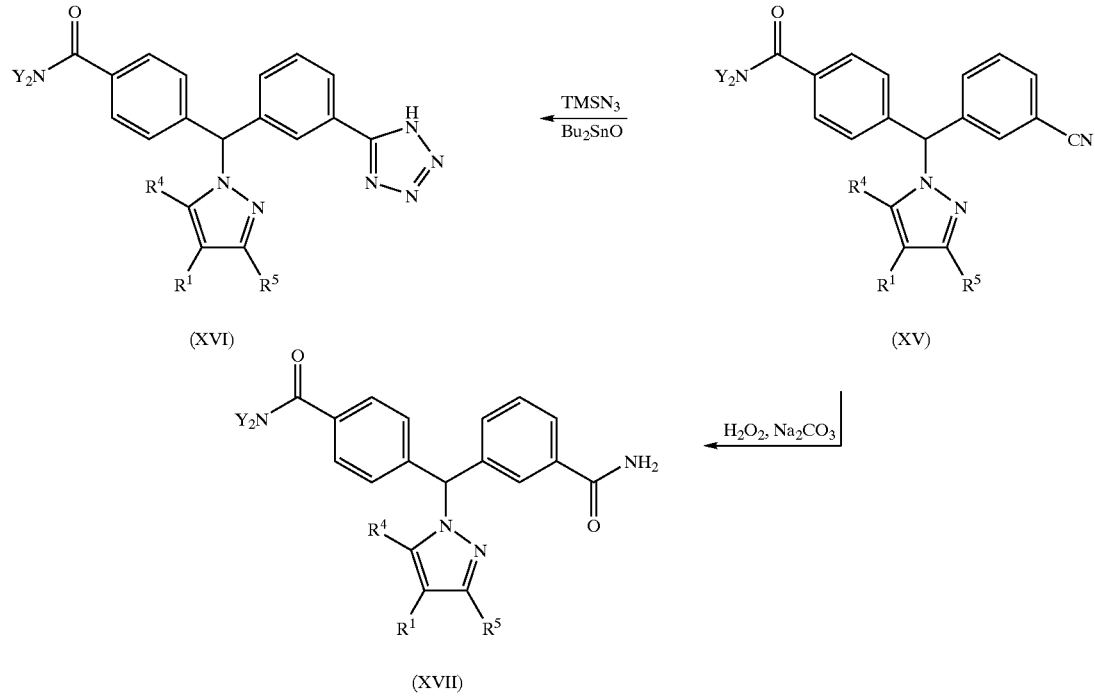

As set forth in Scheme 7, anilines of general formula (XVIII) ($R^3$ is $NH_2$) could be prepared from the sulfonate esters of the general formula (XIV) by treatment with benzophenone imine in the presence of a suitable catalyst (e.g. palladium acetate, BINAP) and base (e.g. sodium tert-butoxide) in toluene, at temperatures ranging from 20° C. to the reflux temperature, preferably at about the reflux temperature. Sulfonamide derivatives of formula (XIX) ($R^3$ is $NHSO_2R^7$) may be prepared by treatment of the corresponding aniline of general formula (XVIII) with alkyl or aryl sulfonyl chlorides (e.g., methane sulfonyl chloride) and an amine base (e.g., pyridine) in solvents such as dichloromethane and dichloroethane, at temperatures ranging from –5° C. to about room temperature, preferably at about room temperature.

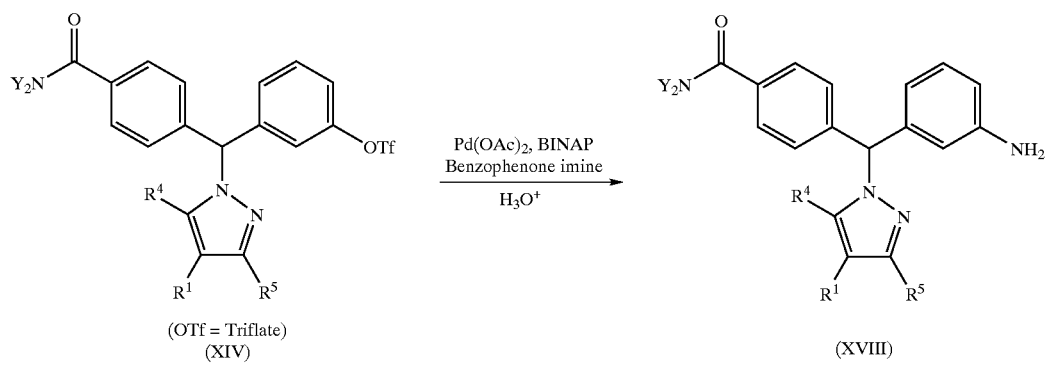

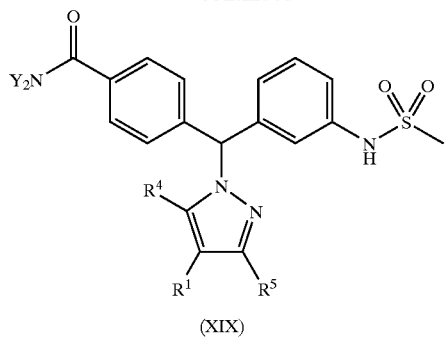

(XIX)

As set forth below in Scheme 8, an ester of general formula (XX) may be produce via placing a sulfonate ester of general formula (XIV) under a carbon monoxide atmosphere at pressures ranging from about 14 to 100 psi, in dimethylsulfoxide and methanol solvent in the presence of palladium acetate, 1,3-bis(diphenylphosphino)propane (dppp) and triethylamine, at temperatures ranging from 20° C. to 100° C. Further treatment of the ester of general formula (XX) with alkyl or aryl lithium or magnesium reagent (e.g. methylmagnesium bromide) in tetrahydrofuran, at temperatures ranging from −78° C. to room temperature, preferably at about 0° C., could produce the tertiary alcohol of general formula (XXI) ($R^3$ is (HO)($R^8$)$_2$C—).

Scheme 8

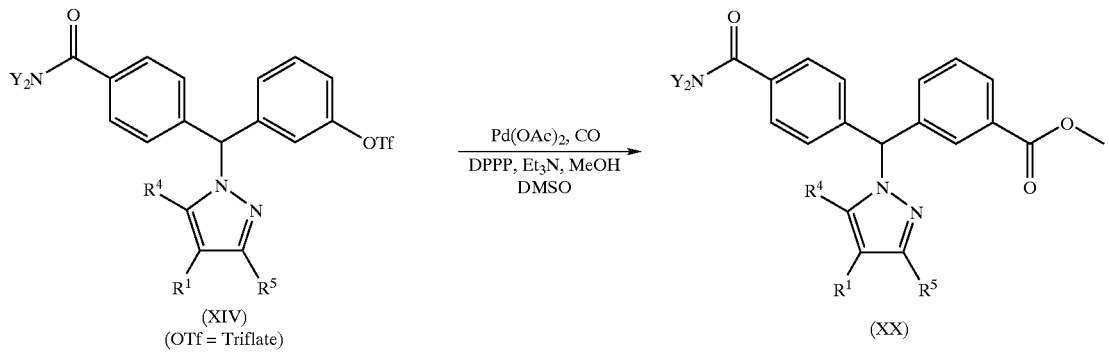

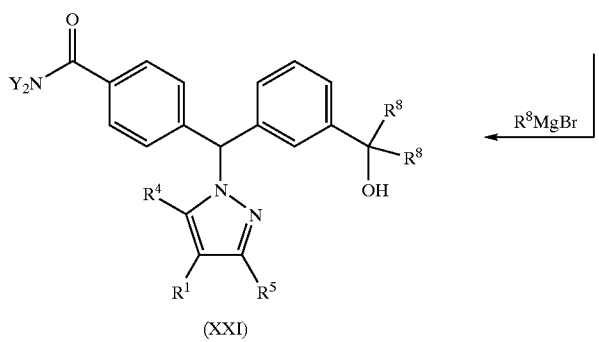

Further, illustrated in Schemes 9 through 10 are means for converting ester compounds of formula (XI) to other compounds of formula (I), i.e., where R² is as defined above. As highlighted in Scheme 9, esters of general formula (XI) (R² is —COOY) can be treated with lithium hydroxide in methanol and water at temperatures ranging from 0° C. to room temperature, preferably at room temperature to afford the corresponding carboxylic acid (not depicted, R² is —COOY). Treatment of the carboxylic acid with oxalyl chloride and a suitable amino alcohol, in dichloromethane or dichloroethane, at temperatures ranging from 0° C. to about room temperature, preferably at about room temperature, produced an hydroxy amide of formula (XXII). Treatment of the hydroxy amide of formula (XXII) with diethylazodicarboxylate (DEAD) and triphenylphosphine in tetrahydrofuran, at temperatures ranging from 0° C. to about room temperature, preferably at about room temperature, could produce the corresponding oxazoline of formula (XXIII) (R² is oxazoline).

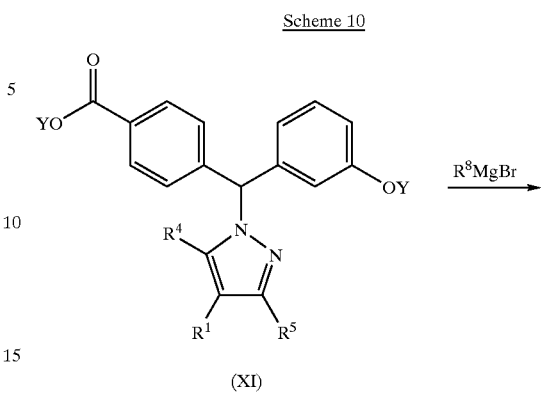

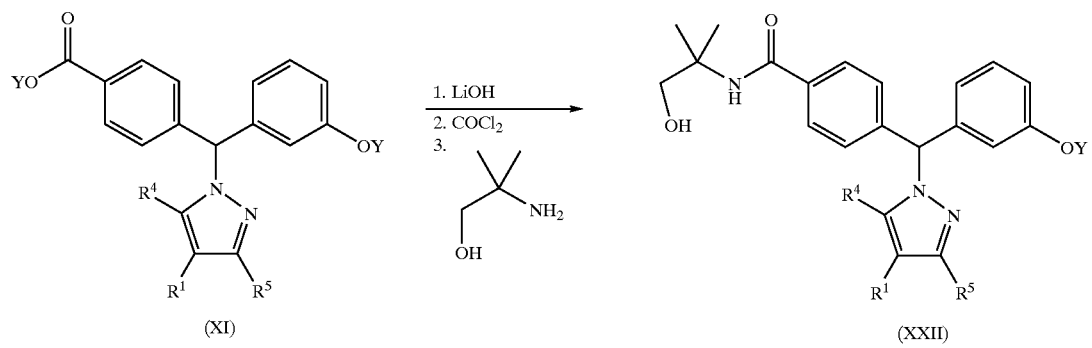

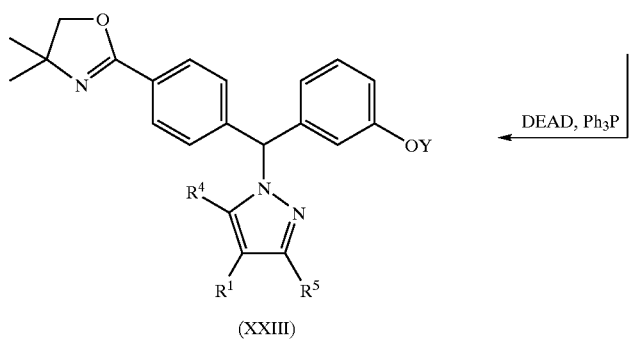

As set forth below in scheme 10, an ester of formula (XI) could be treated with an alkyl or aryl organo-lithium or -magnesium reagent (e.g., methyl magnesium bromide) in tetrahydrofuran, at temperatures ranging from −78° C. to about room temperature, preferably at about 0° C., to afford the correspond alkyl carbinol of formula (XXIV) (R² is —C(OH)(R⁸)₂).

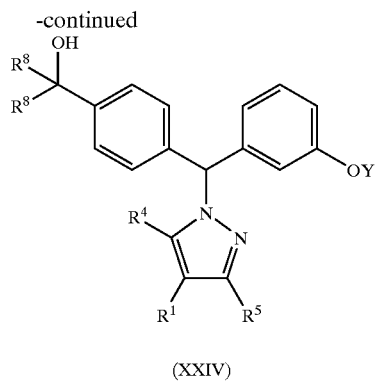

Illustrated below in Schemes 11 and 12 are means for preparing compounds of formula (I), where $R^2$ is halide, aryl, heteroaryl and heterocyclic. Referring to Scheme 11, a 4-bromobenzaldehyde of formula (XXV) can be treated with a magnesium grignard reagent generated from a bromide of formula (XXVI) in a suitable solvent, preferably tetrahydrofuran or diethyl ether, at temperatures ranging from −78° C. to room temperature, preferably at about room temperature, to produce an intermediate benzhydryl alcohol. The intermediate crude benzhydryl alcohol (not depicted) can then treated with thionyl chloride in a suitable solvent, preferably methylene chloride or dichloroethane, at temperatures ranging from room temperature to solvent reflux temperature, preferably at about reflux temperature, which could produce the corresponding benzhydryl chloride of formula (XXVII). The treatment of the chloride of formula (XXVII) with pyrazole of formula (X) and a tetra-alkyl ammonium iodide catalyst, preferably tetra-n-butyl ammonium iodide, in a suitable solvent, preferably acetonitrile, at temperatures ranging from 50° C. to 110° C., preferably at about the reflux temperature of the solvent, may be used to produce the corresponding product of formula (XXVIII). An aryl bromide of formula (XXVIII) could be treated with an aryl or heteroaryl boronic acid or borate ester in the presence of tetrakis(triphenylphosphine)palladium and sodium carbonate as described previously in Scheme 1 to give the compound of formula (XXIX) where $R^2$ is aryl or heteroaryl.

As set forth below in Scheme 12, triazoles of formula (XXX) may be prepared as described previously in Scheme 6. Treatment of the bromide of formula (XVIII) with zinc cyanide in the presence of a suitable catalyst such as tetrakis(triphenylphosphine)palladium in dimethylformamide at temperatures ranging from 20° C. to the reflux temperature, preferably, at about the reflux temperature could afford the intermediate nitrile (not depicted). Tetrazoles of general formula (XXX) could be prepared from the nitrile compound by treatment with azidotrimethylsilane in the presence of a dialkyltin oxide (e.g. dibutyltin oxide) in toluene, at temperatures ranging from about 20° C. to about the reflux temperature, preferably at about reflux.

Scheme 12

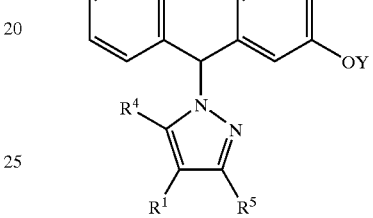

1. Zn(CN)$_2$, Pd(PPh$_3$)$_4$
2. TMSN$_3$, Bu$_2$BuO

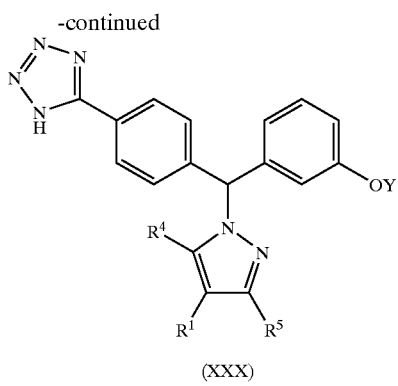

(XXX)

The starting materials used in the processes of Schemes 1 through 12 are either commercially available, known in the literature, or readily obtainable from commercially available or known compounds, or using methods that are well known in the art or described above.

Unless indicated otherwise, the pressure of each of the above reactions is not critical. Generally, the reactions will be conducted at a pressure from about one to about three atmospheres, preferably at ambient pressure (about one atmosphere).

The preparation of other compounds of the formula (I) not specifically described in the foregoing experimental section can be accomplished using combinations of the reactions described above that will be apparent to those skilled in the art.

The present invention also relates to the pharmaceutically acceptable acid addition and base addition salts of compounds of the formula (I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts. The chemical bases that are used as reagents to prepare the pharmaceutically acceptable base salts of this invention are those which form non-toxic base salts with the acidic compounds of formula (I). Such non-toxic base salts include those derived from such pharmacologically acceptable cations as sodium, potassium, calcium and magnesium, etc.

The present invention also relates to the pharmaceutically acceptable base addition salts of compounds of the formula (I). These salts are all prepared by conventional techniques. The chemical bases that are used as reagents to prepare the pharmaceutically acceptable base salts of this invention are those which form non-toxic base salts with the acidic compounds of formula (I). Such non-toxic base salts include those derived from such pharmacologically acceptable cations as sodium, potassium, calcium and magnesium, etc. For a review on pharmaceutically acceptable salts, see Berge et al., *J. Pharm. Sci.*, 66:1–19 (1977).

The compounds of the formula (I) that are basic in nature are capable of forming a wide variety of different salts with various inorganic and organic acids. The acid that can be used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Compounds of the formula that are acidic in nature are capable of forming base salts with various pharmacologically acceptable cations. These salts are all prepared by conventional techniques. The chemical bases that are used as reagents to prepare the pharmaceutically acceptable base salts of this invention are those which form non-toxic base salts with the acidic compounds of formula (I). Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the formula (I) and the pharmaceutically acceptable salts thereof (hereinafter, also referred to, collectively, as "the active compounds of the invention") are useful for the treatment of neurodegenerative disorders, psychotropic disorders, gastrointestinal disorders and drug- or alcohol-induced deficits and are potent opioid receptor ligands. As noted above, the active compounds of the invention may therefore be used in the treatment of diseases disorders and conditions, by modulating binding to an opioid receptor. Examples of diseases, disorders and conditions that can be treated with the compounds of formula (I) and their pharmaceutically acceptable salts are rejection in organ transplants and skin grafts, epilepsy, chronic pain, neurogenic pain, non-somatic pain, stroke, cerebral ischemia, shock, head trauma, spinal cord trauma, brain edema, Hodgkin's disease, Sjogren's disease, systemic lupus erythematosus, gastrointestinal disorders such as gastritis, functional bowel disease, irritable bowel syndrome, functional diarrhea, functional distention, non-ulcerogenic dyspepsia and other disorders of motility or secretion, and emesis, acute pain, chronic pain, neurogenic pain, non-somatic pain, allergies, respiratory disorders such as asthma, cough and apnea, inflammatory disorders such as rheumatoid arthritis, osteoarthritis, psoriasis and inflammatory bowel disease, urogenital tract disorders such as urinary incontinence, hypoxia (e.g., perinatal hypoxia), hypoglycemic neuronal damage, chemical dependencies and addictions (e.g., a dependency on, or addiction to opioid compounds, benzodiazepines, cocaine, nicotine or ethanol), drug or alcohol withdrawal symptoms, and cerebral deficits subsequent to cardiac bypass surgery and grafting.

The ability of the compounds of formula (I) to bind to the various opioid receptors and their functional activity at such receptors can be determined as described below. Binding to the delta opioid receptor can be determined using procedures well known in the art, such as those referred to by Lei Fang et al., *J. Pharm. Exp. Ther.*, 268, 1994, 836–846 and Contreras et al., *Brain Research*, 604, 1993, 160–164.

In the description of binding and functional assays that follows, the following abbreviations and terminology are used. DAMGO is [D-Ala2,N—MePhe4,Gly5-ol] enkephalin); U69593 is ((5a, 7a, 8b)-(+)-N-methyl-N-(7-[1-pyrrolidinyl]-1-oxasipro[4,5]dec-8-yl)-benzeneacetamide); SNC-80 is (+)-4-[($\alpha$R)-$\alpha$((2S,5R)-4-allyl-2,5-dimethyl-1-piperazinyl)-3-methoxybenzyl]-N,N-diethylbenzamide; nor BNI is nor-binaltorphimine; CTOP is 1,2-Dithia-5,8,11,14, 17-pentaazacycloeicosane; and cyclic peptide derivative DPDPE is [D-en2,D-Pen5]enkephalin). [3H]-DAMGO, [3H]-U69593, norBNI, and CTOP are all commercially available from DuPont, Amersham International, RBI and DuPont, Amersham International, RBI and DuPont respectively. [3H]-SNC80 was prepared by Amersham International.

Opioid (mu and kappa) receptor binding assays can be performed in guinea-pig brain membrane preparations. Binding assays can be carried out at 25° C. for 60 minutes in 50 mM Tris (pH 7.4) buffer. [$^3$H]-DAMGO(2 nM) and [$^3$H]-U-69,593 (2 nM) can be used to label mu and kappa receptor binding sites, respectively. The protein concentration can be approximately 200 $\mu$g/well. Non-specific binding can be defined with 10 $\mu$M naloxone.

Delta receptor binding assays can be performed in a stable line of CHO cells expressing the human delta receptor. The binding assay can be carried out at 25° C. for 120 minutes in 50 mM Tris (pH 7.4) buffer. [$^3$H]-SNC-80 can be used to label delta receptor binding sites. The protein concentration can be approximately 12.5 $\mu$g/well. Non-specific binding can be defined with 10 $\mu$M naltrexone.

The binding reaction can be terminated by rapid filtration through glass fiber filters, and the samples can be washed with ice-cold 50 mM Tris buffer (pH 7.4).

Agonist activity at the delta, mu and kappa opioid receptors can be determined as follows.

Opioid (delta, mu and kappa) activity is studied, as described below, in two isolated tissues, the mouse deferens (MVD)($\delta$) and the guinea-pig myentric plexus with attached longitudinal muscle (GPMP) ($\mu$ and k).

MVD (DC1 strain, Charles River, 25–35 g) are suspended in 15 ml organ baths containing $Mg^{++}$ free Krebs' buffer of the following composition (mM): NaCl, 119; KCl, 4.7; $NaHCO_3$, 25; $KH_2PO_4$, 1.2; $CaCl_2$, 2,5 and glucose, 11. The buffer is gassed with 95% $0_2$ and 5% $CO_2$. The tissues are suspended between platinum electrodes, attached to an isometric transducer with 500 mg tension and stimulated with 0.03 Hz pulses of 1-msec pulse-width at supramaximal voltage. $IC_{50}$ values are determined by the regression analysis of concentration-response curves for inhibition of electrically-induced contractions in the presence of 300 nM of the mu-selective antagonist CTOP. This test is a measure of $\delta$ agonism.

Guinea-pig (Porcellus strain, male, 450–500 g, Dunkin Hartley) myentric plexus with attached longitudinal muscle segments are suspended with 1 g of tension in Krebs' buffer and stimulated with 0.1 Hz pulses of 1-msec pulse-width at supramaximal voltage. Mu functional activity is determined in the presence of 10 nM nor-BNI with 1 $\mu$M of the mu selective agonist, DAMGO, added to the bath at the end of the experiment to define a maximal response. This test is a measure of mu agonism.

Kappa functional activity is determined in the presence of and 1 $\mu$M CTOP with 1 $\mu$M of the kappa selective agonist U-69,593 added at the end of the experiment to define a maximal response. All inhibitions of twitch height for test compounds are expressed as a percentage of the inhibition obtained with the standard agonist and the corresponding $IC_{50}$ values determined.

The following procedure can be used to determine the activity of the therapeutic agents of this invention as agonists and as antagonists of delta opioid receptors.

Cell Culture: Chinese hamster ovary cells expressing the human delta opioid receptor are passaged twice weekly in Hamis F-12 media with L-glutamine containing 10% fetal bovine serum and 450 $\mu$g/mL hygromycin. Cells are prepared for assays 3 days prior to the experiment. 15 mL of 0.05% trypsin/EDTA is added to a confluent triple flask, swirled and decanted to rinse. 15 mL of 0.05% trypsin/EDTA is again added, and the flask is placed into a 37 C. incubator for 2 minutes. Cells are removed from the flask by banking, and supernatant poured off into a 50 mL tube. 30 mL of media is then added to the flask to stop the action of the trypsin, and then decanted into the 50 mL tube. Tube is then centrifuged for 5 minutes at 1000 rpm, media decanted, and the pellet resuspended into 10 mL of media. Viability of the cells is assessed using trypan blue, the cells counted and plated out into 96 well poly-D-lysine coated plates at a density of 7,500 cells/well.

Antagonist Test Plate: Cells plated 3 days prior to assay are rinsed twice with PBS. The plates are placed into a 37 C. water bath. 50 $\mu$L of assay buffer (PBS, dextrose 1 mg/mL, 5 mM MgC12, 30 mM HEPES, 66.7 $\mu$g/mL of IBMX) is then added to designated wells. Fifty microliters of appropriate drug is then added to designated wells, and timed for 1 minute. Fifty microliters of 10 $\mu$M forskolin+0.4 nM DPDPE (final assay concentration is 5 $\mu$M forskolin, 0.2 nM DPDPE) is then added to appropriate wells, and timed for 15 minutes. The reaction is stopped by the addition of 10 $\mu$L of 6N perchloric acid to all wells. To neutralize, 13 $\mu$L of 5N KOH is added to all wells, and to stabilize 12 $\mu$L of 2M Tris, pH 7.4 is added to all wells. Mix by shaking on an orbital shaker for 10 minutes, and centrifuge at setting 7 for 10 minutes. Aliquot into 3H plate.

Agonist Test Plate: Cells plated 3 days prior to assay are rinsed twice with PBS. The plates are placed into a 37° C. water bath. Fifty microliters of assay buffer (PBS, dextrose 1 mg/mL, 5 mM $MgCl_2$, 30 mM HEPES, 66.7 $\mu$g/mL of IBMX) is then added to designated wells. Fifty microliters of appropriate drug+10 $\mu$M forskolin (final assay concentration is 5 $\mu$M forskolin) is then added to all wells, and timed for 15 minutes. The reaction is then stopped by the addition of 10 $\mu$L of 6N perchloric acid to all wells. To neutralize, 13$\mu$ of 5N KOH is added to all wells, and to stabilize 12 $\mu$L of 2M Tris, pH 7.4 is added to all wells. Mix by shaking on an orbital shaker for 10 minutes, and centrifuge at setting 7 for 10 minutes. Aliquot into 3H plate.

Both test plates are placed into an Amersham 3H cAMP binding kit overnight, and harvested onto GF/B filters previously soaked in 0.5% PEI with a Skatron using 50 mM Tris HCl pH 7.4 at 4° C. Filtermats can be air-dried overnight then place in bags with 20 ml Betaplate scintillation cocktail and counted on a Betaplate counter for 60 sec per sample. Data can be analyzed using Excel.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

In general, a therapeutically effective daily oral or intravenous dose of the compounds of formula (I) and their salts is likely to range from 0.001 to 50 mg/kg body weight of the subject to be treated, preferably 0.1 to 20 mg/kg. The compounds of the formula (I) and their salts may also be administered by intravenous infusion, at a dose which is likely to range from 0.001–10 mg/kg/hr.

Tables or capsules of the compounds may be administered singly or two or more at a time as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

EXAMPLES

The following Examples illustrate the preparation of the compounds of the present invention. Commercial reagents were utilized without further purification. All NMR data were recorded at 250, 300 or 400 MHz in deuterochloroform unless otherwise specified and are reported in parts per million (δ) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C.

Example 1

N,N-Diethyl-4-[[4-(4-fluoro-phenyl)-3,5-dimethyl-pyrazol-1-yl]-(3-methoxy-phenyl)-methyl]-benzamide A. N,N-Diethyl-4-[(4-iodo-3,5-dimethyl-pyrazol-1-yl)-(3-methoxy-phenyl)-methyl]-benzamide To a stirring solution of 4-[Chloro-(3-methoxy-phenyl)-methyl]-N,N-diethyl-benzamide (1.11 g, 3.32 mmol) in 20 Ml $CH_3CN$ was added 4-iodo-3,5-dimethyl pyrazole (1.64 g, 7.40 mmol) and tetra-n-butyl ammonium iodide (619 mg, 1.68 mmol). The mixture was heated to reflux for 24 h, cooled to room temperature and concentrated under reduce pressure. The crude oil was purified by flash chromatography on a 3×20 cm column, eluting with 30% ethyl acetate/hexanes, collecting 8 mL fractions. The product containing fractions were collected and concentrated under reduce pressure to give the desired product (1.65 g, 96%) as a clear yellow oil. 400 MHz $^1$H NMR ($CDCl_3$) δ 7.31 (d, J=8.1 Hz, 2H), 7.19–7.24 (m, 1H), 7.13 (d, J=8.3 Hz, 2H), 6.79–6.82 (m, 1H), 6.68–6.70 (m, 2H), 6.54 (s, 1H), 3.71 (s, 3H), 3.50

(br s, 2H), 3.23 (br s, 2H), 2.21 (s, 3H), 2.18 (s, 3H), 1.21 (br s, 3H), 1.08 (br s, 3H); 75 MHz $^{13}$C NMR (CDCl$_3$), δ 170.8, 159.7, 149.8, 141.2, 140.3, 140.1, 136.7, 129.6, 128.5, 126.6, 120.8, 114.4, 113.2, 66.5, 55.3, 43.3, 39.3, 14.4, 12.6; MS (M+1) 518.0.

B. N,N-Diethyl-4-[[4-(4-fluorophenyl)-3,5-dimethylpyrazol-1-yl]-(3-methoxyphenyl)-methyl]-benzamide To a stirring solution of N,N-Diethyl-4-[(4-iodo-3,5-dimethyl-pyrazol-1-yl)-(3-methoxy-phenyl)-methyl]-benzamide (145 mg, 0.281 mmol) in 20 Ml EtOH/H$_2$O (9:1) at room temperature was added 4-fluorobenzene boronic acid (118 mg, 0.842 mmol), Na$_2$CO$_3$ (90.0 mg, 0.842 mmol) and tetrakis(triphenylphosphine) palladium (0) (30.0 mg, 0.005 mmol). The mixture was cooled to −78° C., de-oxygenated under reduced pressure and purged with nitrogen gas. The mixture was refluxed for 2 hours, cooled to room temperature, filtered through a Celite pad and concentrated under reduce pressure. Purification of the crude material was accomplished by flash chromatography on a 2×15 cm column, eluting with 30% ethyl acetate/hexanes, collecting 8 Ml fractions. The product containing fractions were collected and concentrated to give the desired product (120 mg, 88%) as a clear colorless solid. 300 MHz $^1$H NMR (CDCl$_3$) δ 7.33 (d, J=8.3 Hz, 2H), 7.16–7.23 (m, 5H), 7.04–7.15 (m, 2H), 6.71–6.84 (m, 3H), 6.55 (s, 1H), 3.74 (s, 3H), 3.52 (br s, 2H), 3.27 (br s, 2H), 2.19 (s, 3H), 2.16 (s, 3H), 1.21 (br s, 3H), 1.09 (br s, 3H), MS (M+1) 486.2.

The following compounds were made using the procedure of Example 1:

4-[(3,5-Dimethyl-pyrazol-1-yl)-phenyl-methyl]-N,N-diethyl-benzamide 400 MHz $^1$H NMR (CDCl$_3$) δ 7.21–7.33 (m, 5H), 7.11–7.13 (m, 4H), 6.53 (s, 1H), 5.83 (s, 1H), 3.49 (brs, 2H), 3.23 (brs, 2H), 2.18 (s, 3H), 2.13 (s, 3H), 1.21 (brs, 3H), 1.07 (brs, 3H); MS (M+1) 362.2.

4-[(3,5-Dimethyl-pyrazol-1-yl)-(3-fluoro-phenyl)-methyl]-N,N-diethyl-benzamide 400 MHz $^1$H NMR (CDCl$_3$) δ 7.31 (d, J=6.6 Hz, 2H), 7.22–7.29 (m, 1H), 7.14 (d, J=7.9 Hz, 2H), 6.82–6.96 (m, 3H), 6.49 (s, 1H), 5.84 (s, 1H), 3.49 (brs, 2H), 3.23 (brs, 2H), 2.18 (s, 3H), 2.15 (s, 3H), 1.22 (brs, 3H), 1.19 (brs, 3H); MS (M+1) 380.2.

Example 2

Deprotection Of Methyl Aryl Ethers

A solution of the methyl ether (1 equiv.) in 47% HBr solution (0.05 M) was heated at gentle reflux for 1–3 h. The reaction was cooled to room temperature, slowly poured into NH$_4$OH, and diluted with ethyl acetate. The layers were separated, the aqueous layer was extracted with ethyl acetate, the combined organic layers dried over anhydrous Na$_2$SO$_4$ and concentrated under reduce pressure. The crude material was purified by flash chromatography to afford the desired phenols in yields ranging from 50–86%.

Alternatively, the methyl ethers were deprotected with sodium hydride and ethane thiol in DMF as follows:

To a suspension of NaH (10 equivalents) in DMF (0.2M) at room temperature was added ethane thiol (10 equivalents) dropwise. The mixture was stirred for 5 minutes. To the reaction mixture was added a solution of the methyl ether (1 equivalent) in DMF (0.2M). The mixture was heated to 120° C. for 10–16 hours. The reaction was cooled to room temperature and was quenched with water. The mixture was diluted with diethyl ether and the organic layer was washed with brine. The organic phase was dried (MgSO$_4$) and concentrated. Purification by flash chromatography afforded the desired phenols in yields ranging from 60–95%.

The following compounds were made using the procedure of Example 2.

N,N-Diethyl-4-[[4-(4-fluoro-phenyl)-3,5-dimethyl-pyrazol-1-yl]-(3-hydroxy-phenyl)-methyl]-benzamide. 400 MHz $^1$H NMR (CDCl$_3$) δ 8.50 (br s, 1H), 7.31 (d, J=8.3 Hz, 2H), 6.95–7.17 (m, 7H), 6.72 (s, 1H), 6.65 (d, J=7.7 Hz, 1H), 6.53–6.56 (m, 2H), 3.52 (br s, 2H), 3.33 (br s, 2H), 2.17 (s, 3H), 1.93 (s, 3H), 1.24 (br s, 3H), 1.10 (br s, 3H); MS (M+1) 472.2.

4-[(4-Bromo-3,5-dimethyl-pyrazol-1-yl)-(3-hydroxy-phenyl)-methyl]-N,N-diethyl-benzamide. 300 MHz $^1$H NMR (CDCl$_3$) δ 7.25–7.40 (m, 2H), 7.10–7.19 (m, 3H), 6.61–6.70 (m, 2H), 6.40–6.51 (m, 2H), 3.51 (br s, 2H), 3.32 (br s, 2H), 2.23 (s, 3H), 2.02 (s, 3H), 1.25 (br s, 3H), 1.05 (br s, 3H); MS (M+1) 458.1.

N,N-Diethyl-4-[(3-hydroxy-phenyl)-(4-iodo-3,5-dimethyl-pyrazol-1-yl)-methyl]-benzamide. 300 MHz $^1$H NMR (CDCl$_3$) δ 7.28 (d, J=8.1 Hz, 2H), 7.06–7.16 (m, 3H), 6.43–6.60 (m, 4H), 3.51 (br s, 2H), 3.30 (br s, 2H), 2.20 (s, 3H), 1.97 (s, 3H), 1.23 (br s, 3H), 1.09 (br s, 3H); MS (M+1) 504.1.

4-[(3,5-Dimethyl-4-phenyl-pyrazol-1-yl)-(3-hydroxy-phenyl)-methyl]-N,N-diethyl-benzamide. 400 MHz $^1$H NMR (CDCl$_3$) δ 7.08–7.34 (m, 10H), 6.76 (s, 1H), 6.66 (d, J=7.5 Hz, 1H), 6.61 (s, 1H), 6.55 (d, J=8.3 Hz, 1H), 3.53 (br s, 2H), 3.34 (br s, 2H), 2.19 (s, 3H), 1.98 (s, 3H), 1.24 (br s, 3H), 1.10 (br s, 3H); MS (M+1) 454.2.

N,N-Diethyl-4-{(3-hydroxy-phenyl)-[4-(4-hydroxy-phenyl)-3,5-dimethyl-pyrazol-1-yl]-methyl}-benzamide. 400 MHz $^1$H NMR (CDCl$_{13}$) δ 7.31 (d, J=7.9 Hz, 2H), 7.08–7.16 (m, 3H), 6.84 (d, J=8.3 Hz, 2H), 6.70–6.75 (m, 3H), 6.65 (d, J=7.5 Hz, 1H), 6.58 (s, 2H), 3.53 (br s, 2H), 3.33 (br s, 2H), 2.13 (s, 3H), 1.89 (s, 3H), 1.25 (br s, 3H), 1.11 (br s, 3H); MS (M+1) 470.2.

4-[[4-(4-Chloro-phenyl)-3,5-dimethyl-pyrazol-1-yl]-(3-hydroxy-phenyl)-methyl]-N,N-diethyl-benzamide. 400 MHz $^1$H NMR (CDCl$_3$) δ 7.03–7.67 (m, 10H), 6.51–6.71 (m, 3H), 3.53 (br s, 2H), 3.33 (br s, 2H), 2.18 (s, 3H), 1.96 (s, 3H), 1.24 (br s, 3H), 1.11 (br s, 3H); MS (M+1)??.

4-[(3,5-Dimethyl-4-p-tolyl-pyrazol-1-yl)-(3-hydroxy-phenyl)-methyl]-N,N-diethyl-benzamide. 400 MHz $^1$H NMR (CDCl$_3$) δ 7.31 (d, J=8.1 Hz, 2H), 7.08–7.18 (m, 5H), 6.97 (d, J=7.9 Hz, 2H), 6.75 (s, 1H), 6.65 (d, J=7.7 Hz, 1H), 6.61 (s, 1H), 6.55–6.58 (m, 1H), 3.52 (br s, 2H), 3.33 (br s, 2H), 2.36 (s, 3H), 2.18 (s, 3H), 1.98 (s, 3H), 1.23 (br s, 3H), 1.10 (br s, 3H); MS (M+1) 468.2.

4-[[3,5-Dimethyl-4-(4-trifluoromethyl-phenyl)-pyrazol-1-yl]-(3-hydroxy-phenyl)-methyl]-N,N-diethyl-benzamide. 400 MHz $^1$H NMR (CDCl$_3$) δ 7.55 (d, J=8.1 Hz, 2H), 7.33 (d, J=8.1 Hz, 2H), 7.14–7.26 (m, 5H), 6.70–6.73 (m, 2H), 6.63 (d, J=8.3 Hz, 1H), 6.57 (s, 1H), 3.53 (br s, 2H), 3.32 (br s, 2H), 2.22 (s, 3H), 2.04 (s, 3H), 1.23 (br s, 3H), 1.11 (br s, 3H); MS (M+1) 522.2.

4-[[4-(3-Chloro-4-fluoro-phenyl)-3,5-dimethyl-pyrazol-1-yl]-(3-hydroxy-phenyl)-methyl]-N,N-diethyl-benzamide. 400 MHz $^1$H NMR (CDCl$_3$) δ 7.31 (d, J=7.9 Hz, 2H), 7.06–7.22 (m, 5H), 6.95–6.98 (m, 1H), 6.65–6.70 (m, 2H), 6.59 (d, J=8.1 Hz, 1H), 6.54 (s, 1H), 3.52 (br s, 2H), 3.30 (br s, 2H), 2.17 (s, 3H), 2.01 (s, 3H), 1.22 (br s, 3H), 1.09 (br s, 3H); MS (M+1) 506.2.

4-[(3,5-Dimethyl-4-m-tolyl-pyrazol-1-yl)-(3-hydroxy-phenyl)-methyl]-N,N-diethyl-benzamide. 400 MHz $^1$H NMR (CDCl$_3$) δ 7.04–7.32 (m, 7H), 6.93 (s, 1H), 6.85 (d, J=6.4 Hz, 1H), 6.76 (s, 1H), 6.65 (d, J=5.2 Hz, 1H), 6.52–6.54 (m, 2H), 3.53 (br s, 2H), 3.34 (br s, 2H), 2.27 (s, 3H), 2.19 (s, 3H), 1.95 (s, 3H), 1.23 (br s, 3H), 1.10 (br s, 3H); MS (M+1) 468.2.

4-[(3,5-Dimethyl-4-o-tolyl-pyrazol-1-yl)-(3-hydroxy-phenyl)-methyl]-N,N-diethyl-benzamide. 400 MHz $^1$H NMR (CDCl$_3$) δ 7.63–7.68 (m, 1H), 7.44–7.52 (m, 2H), 7.25–7.34 (m, 2H), 6.98–7.22 (m, 5H), 6.52–6.78 (m, 3H), 3.53 (br s, 2H), 3.25 (br s, 2H), 2.08, 2.06 (s, 3H total), 1.99, 1.93 (s, 3H total), 1.24 (s, 3H), 1.20 (br s, 3H), 1.09 (br s, 3H); MS (M+1) 468.3.

4-[[3,5-Dimethyl-4-(3-trifluoromethyl-phenyl)-pyrazol-1-yl]-(3-hydroxy-phenyl)-methyl]-N,N-diethyl-benzamide. 400 MHz $^1$H NMR (CDCl$_3$) δ 8.5 (br s, 1H), 7.48 (d, J=7.9 Hz, 1H), 7.09–7.37 (m, 8H), 6.71 (s, 1H), 6.66 (d, J=7.3 Hz, 1H), 6.54–6.60 (m, 2H), 3.52 (br s, 2H), 3.32 (br s, 2H), 2.19 (s, 3H), 1.98 (s, 3H), 1.24 (br s, 3H), 1.10 (br s, 3H); MS (M+1) 522.4.

4-[[4-(3,5-Bis-trifluoromethyl-phenyl)-3,5-dimethyl-pyrazol-1-yl]-(3-hydroxy-phenyl)-methyl]-N,N-diethyl-benzamide. 400 MHz $^1$H NMR (CDCl$_3$) δ 7.77 (s, 1H), 7.61 (s, 2H), 7.33 (d, J=8.1 Hz, 2H), 7.12–7.20 (m, 3H), 6.63–6.70 (m, 3H), 6.56 (s, 1H), 3.53 (br s, 2H), 3.30 (br s, 2H), 2.21 (s, 3H), 2.11 (s, 3H), 1.25 (br s, 3H), 1.10 (br s, 3H); MS (M+1) 590.2

4-[[4-(3,5-Dichloro-phenyl)-3,5-dimethyl-pyrazol-1-yl]-(3-hydroxy-phenyl)-methyl]-N,N-diethyl-benzamide. 400 MHz $^1$H NMR (CDCl$_3$) δ 7.90 (br s, 1H), 7.30 (s, 2H), 7.09–7.19 (m, 3H), 6.99 (s, 2H), 6.52–6.66 (m, 4H), 3.53 (br s, 2H), 3.30 (br s, 2H), 2.19 (s, 3H), 2.04 (s, 3H), 1.24 (br s, 3H), 1.10 (br s, 3H); MS (M+1) 522.2.

4-[[4-(2,4-Dichloro-phenyl)-3,5-dimethyl-pyrazol-1-yl]-(3-hydroxy-phenyl)-methyl]-N,N-diethyl-benzamide. 400 MHz $^1$H NMR (CDCl$_3$) δ 7.48 (s, 1H), 7.25–7.32 (m, 2H), 7.10–7.23 (m, 5H), 6.59–6.70 (m, 4H), 3.46 (br s, 2H), 3.24 (br s, 2H), 2.03 (s, 6H), 1.24 (br s, 3H), 1.09 (br s, 3H); MS (M+1) 522.2.

N,N-Diethyl-4-[(4-furan-2-yl-3,5-dimethyl-pyrazol-1-yl )-(3-hydroxy-phenyl)-methyl]-benzamide. 400 MHz $^1$H NMR (CDCl$_3$) δ 7.91 (br s, 1H), 7.38 (s, 1H), 7.29–7.31 (m, 2H), 7.09–7.15 (m, 3H), 6.64 (d, J=7.3 Hz, 1H), 6.43–6.58 (m, 3H), 6.40 (s, 1H), 6.10 (d, J=3.1 Hz, 1H), 3.52 (br s, 2H), 3.31 (br s, 2H), 2.15 (s, 3H), 2.05 (s, 3H), 1.24 (br s, 3H), 1.09 (br s, 3H); MS (M+1) 444.2.

4-[(3,5-Dimethyl-4-thiophen-2-yl-pyrazol-1-yl)-(3-hydroxy-phenyl)-methyl]-N,N-diethyl-benzamide. 400 MHz $^1$H NMR (CDCl$_3$) δ 7.05–7.71 (m, 8H), 6.55–6.91 (m, 4H), 3.51 (br s, 2H), 3.32 (br s, 2H), 2.21 (s, 3H), 2.05 (s, 3H), 1.24 (br s, 3H), 1.09 (br s, 3H); MS (M+1) 460.2.

4-[(3,5-Dimethyl-4-thiophen-3-yl-pyrazol-1-yl)-(3-hydroxy-phenyl)-methyl]-N,N-diethyl-benzamide. 400 MHz $^1$H NMR (CDCl$_3$) δ 8.92 (br s, 1H), 7.30 (s, 3H), 7.08–7.19 (m, 3H), 6.89 (d, J=4.6 Hz, 1H), 6.84 (s, 1H), 6.63–6.68 (m, 2H), 6.51–6.55 (m, 2H), 3.53 (br s, 2H), 3.36 (br s, 2H), 2.22 (s, 3H), 1.90 (s, 3H), 1.24 (br s, 3H), 1.11 (br s, 3H); MS (M+1) 460.2.

4-[(3,5-Dimethyl-4-naphthalen-1-yl-pyrazol-1-yl)-(3-hydroxy-phenyl)-methyl]-N,N-diethyl-benzamide. 400 MHz $^1$H NMR (CDCl$_3$) δ 7.78–7.91 (m, 2H), 7.05–7.59 (m, 10H), 6.87 (s, 1H), 6.73 (d, J=7.1 Hz, 1H), 6.51–6.68 (m, 2H), 3.55 (br s, 2H), 3.31 (br s, 2H), 2.15 (s, 3H), 1.95 (s, 3H), 1.24 (br s, 3H), 1.08 (br s, 3H); MS(M+1) 504.3.

(−)-4-[(3,5-Dimethyl-pyrazol-1-yl)-(3-hydroxy-phenyl)-methyl]-N,N-diethyl-benzamide α$_D$=−137.1 (c 0.43, CHCl$_3$), MS (M+1) 378.2.

(+)-4-[(3,5-Dimethyl-pyrazol-1-yl)-(3-hydroxy-phenyl)-methyl]-N,N-diethyl-benzamide α$_D$=+133.5 (c 0.42, CHCl$_3$), MS (M+1) 378.2.

Example 3

A. 4-[Chloro-(3-methoxy-phenyl)-methyl]-benzoic acid methyl ester

To a stirring solution of magnesium metal (3.7 g, 143 mmol) in 300 mL tetrahydrofuran at room temperature was added 3-bromoanisole (20 g, 107 mmol) dropwise. After complete addition the reaction was heated at 80° C. for 3 hours, cooled to −78° C. and added via cannula to a solution of 4-formylbenzoate (12 g, 71 mmol) in 100 mL tetrahydrofuran at −78° C. The solution was allowed to slowly warmed to room temperature over 6 hours. The reaction was quenched by the addition of aqueous ammonium chloride solution and diluted with ethyl ether. The layers were separated and the aqueous layer was extracted with diethyl ether. The combined organic layers were washed with brine, dried over anhydrous magnesium sulfate and concentrated under reduce pressure. The resulting crude alcohol was used in the next step without further purification.

To a stirring solution of the alcohol prepared above in 180 mL of dichloromethane at room temperature was added thionyl chloride (54.7 g, 460 mmol). The mixture was refluxed for 2 hours, cooled to room temperature and concentrated under reduced pressure. The resulting crude material was purified by flash chromatography with 35% ethyl acetate/hexanes. The product containing fractions were collected and concentrated to yield 19.1 g (92%) of the desired product as a yellow oil. 400 MHz $^1$H NMR (CDCl$_3$) δ 7.98–8.01 (m, 2H), 7.46–7.49 (m, 2H), 7.22–7.27 (m, 1H), 6.92–6.95 (m, 2H), 6.81–6.84 (m, 1H), 6.09 (s, 1H), 3.90 (s, 3H), 3.77 (s, 3H); MS (M+1) 255.2 (—HCl).

B. 4-[(3,5-Dimethyl-pyrazol-1-yl)-(3-methoxy-phenyl)-methyl]-benzoic acid methyl ester To a stirring solution of 4-[Chloro-(3-methoxy-phenyl)-methyl]-benzoic acid methyl ester (5.0 g, 17.3 mmol) in 87 mL CH$_3$CN was added 3,5-dimethyl pyrazole (5.0 g, 51.8 mmol) and tetra-n-butyl ammonium iodide (3.2 g, 8.6 mmol). The mixture was heated to reflux for 24 h, cooled to room temperature and concentrated under reduce pressure. The crude oil was purified by flash chromatography with 30% ethyl acetate/hexanes, collecting 8 mL fractions. The product containing fractions were collected and concentrated under reduce pressure to give the desired product (1.8 g, 30%) as a clear yellow oil. 400 MHz $^1$H NMR (CDCl$_3$) δ 7.97 (d, J=8.5 Hz, 2H), 7.19–7.25 (m, 3H), 6.81–6.83 (m, 1H), 6.68–6.73 (m, 2H), 6.52 (s, 1H), 5.85 (s, 1H), 3.89 (s, 3H), 3.72 (s, 3H), 2.20 (s, 3H), 2.16 (s, 3H); MS (M+1) 351.2.

Example 4

4-[(3,5-Dimethyl-pyrazol-1-yl)-(3-hydroxy-phenyl)-methyl]-N,N-dimethyl-benzamide To a stirring suspension of dimethyl amine hydrochloride (233 mg, 2.88 mmol) in 1,2-dichloroethane (10 mL) at 0° C. was added a 2.0 M solution of AlMe$_3$ (1.4 mL, 2.88 mmol) dropwise. The resulting mixture stirred at room temperature for 1 hour. A solution of 4-[(3,5-Dimethyl-pyrazol-1-yl)-(3-methoxy-phenyl)-methyl]-benzoic acid methyl ester (200 mg, 0.57 mmol) in 2 mL 1,2-dichloroethane was added and the mixture was heated to 85° C. for 16 hours. The reaction was cooled to room temperature, slowly poured into a saturated solution of Rochelle salts (20 mL) and diluted with CH$_2$Cl$_2$ (20 mL). The layers were separated, the aqueous layer was extracted with CH$_2$Cl$_2$ (3×10 mL) and the combined organic layers were dried and concentrated.

The crude amide was dissolved in 2 mL 40% hydrobromic acid and 2 mL glacial acetic acid and heated to mild reflux for 2 hours. The reaction was cooled to room temperature, poured slowly into a cold aqueous solution of ammonium hydroxide and diluted with methylene chloride. The layers were separated, the aqueous layer was extracted with methylene chloride and the combined organic layers were dried and concentrated. The resulting crude material was purified by flash chromatography with 80% ethyl acetate/hexanes to give 60 mg, (30% yield over two steps) of the desired phenol. 400 MHz $^1$H NMR (CDCl$_3$) δ 9.20 (brs, 1H), 7.31 (d, J=8.3 Hz, 2H), 7.02–7.11 (m, 3H), 6.56 (d, J=7.7 Hz, 1H), 6.43–6.49 (m, 3H), 5.83 (s, 1H), 3.08 (brs, 3H), 3.02 (brs, 3H), 2.15 (s, 3H), 1.89 (s, 3H); MS (M+1) 350.4.

The following compounds were made using the procedure of Example 4.

4-[(3,5-Dimethyl-pyrazol-1-yl)-(3-hydroxy-phenyl)-methyl]-N,N-dipropyl-benzamide 400 MHz $^1$H NMR (CDCl$_3$) δ 9.01 (brs, 1H), 7.24–7.27 (m, 2H), 7.03–7.11 (m, 3H), 6.42–6.54 (m, 4H), 5.83 (s, 1H), 3.42–3.43 (m, 2H), 3.19–3.24 (m, 2H), 2.13 (s, 3H), 1.94 (s, 3H), 1.65–1.67 (m, 2H), 1.51–1.53 (m, 2H), 0.94 (brs, 3H), 0.74 (brs, 3H); MS (M+1) 406.2.

N,N-Diethyl-4-[(3-hydroxy-phenyl)-pyrazol-1-yl-methyl]-benzamide. 400 MHz $^1$H NMR (CDCl$_3$) δ 7.54 (s, 1H), 7.24–7.28 (m, 2H), 7.20 (s, 1H), 7.01–7.19 (m, 3H), 6.67 (d, J=7.5 Hz, 1H), 6.63 (s, 1H), 3.50 (br s, 2H), 3.22 (br s, 2H), 1.21 (s, 3H), 1.07 (br s, 3H); MS (M+1) 350.2.

4-[(3,5-Dimethyl-pyrazol-1-yl)-(3-hydroxy-phenyl)-methyl]-N,N-diethyl-benzamide. 300 MHz $^1$H NMR (CDCl$_3$) δ 8.70 (br s, 1H), 7.27 (d, J=7.9 Hz, 2H), 7.02–7.24 (m, 3H) 6.55 (d, J=7.7 Hz, 1H), 6.45–6.49 (m, 3H), 5.82 (s, 1H), 3.50 (br s, 2H), 3.29 (br s, 2H), 2.13 (s, 3H), 1.92 (s, 3H), 1.21 (br s, 3H), 1.08 (br s, 3H); 75 MHz $^{13}$C NMR (CDCl$_3$) δ 171.1, 158.1, 147.9, 140.4, 139.9, 139.6, 136.5, 129.4, 128.9, 126.5, 118.9, 115.4, 114.5, 106.1, 65.2, 43.4, 39.2, 12.9, 11.5; MS (M+1) 378.2.

Azepan-1-yl-{4-[(3,5-dimethyl-pyrazol-1-yl)-(3-hydroxy-phenyl)-methyl]-phenyl-methanone 400 MHz $^1$H NMR (CDCl$_3$) δ 9.18 (brs, 1H), 7.26–7.29 (m, 2H), 7.01–7.10 (m, 3H), 6.54 (d, J=7.7 Hz, 1H), 6.44–6.48 (m, 3H), 5.82 (s, 1H), 3.62–3.65 (m, 2H), 3.41–3.44 (m, 2H), 2.13 (s, 3H), 1.92 (s, 3H), 1.78–1.80 (m, 2H), 1.56–1.59 (m, 6H); MS (M+1) 404.3.

(3,4-Dihydro-1H-isoquinolin-2-yl)-{4-[(3,5-dimethyl-pyrazol-1-yl)-(3-hydroxy-phenyl)-methyl]-phenyl}-methanone 400 MHz $^1$H NMR (CDCl$_3$) δ 7.36–7.38 (m, 2H), 7.15–7.26 (m, 7H), 6.51–6.98 (m, 4H), 5.87 (s, 1H), 4.86 (brs, 1.4H), 4.66 (brs, 0.6H), 3.97 (brs, 0.6H), 3.69 (brs, 1.4H), 2.97 (brs, 0.6H), 2.85 (brs, 1.4H), 2.16 (s, 3H), 1.98 (s, 3H); MS (M+1) 438.2.

N,N-Dibutyl-4-[(3,5-dimethyl-pyrazol-1-yl)-(3-hydroxy-phenyl)-methyl]-benzamide 400 MHz $^1$H NMR (CDCl$_3$) δ 7.26 (d, J=8.1 Hz, 2H), 7.10 (d, J=8.1 Hz, 2H), 7.05 (t, J=7.9 Hz, 1H), 6.50–6.54 (m, 2H), 6.46 (s, 1H), 6.41 (s, 1H), 5.83 (s, 1H), 3.44–3.46 (m, 2H), 3.20–3.28 (m, 2H), 2.39–2.44 (m, 4H), 2.13 (s, 3H), 1.97 (s, 3H), 1.75–1.84 (m, 2H), 1.61–1.68 (m, 2H), 0.97–0.99 (m, 3H), 0.75–0.82 (m, 3H); MS (M+1) 434.2.

4-[(3,5-Dimethyl-pyrazol-1-yl)-(3-hydroxy-phenyl)-methyl]-N,N-diisopropyl-benzamide 400 MHz $^1$H NMR (CDCl$_3$) δ 7.22–7.26 (m, 2H), 6.98–7.14 (m, 3H), 6.49–6.57 (m, 3H), 6.45 (s, 1H), 5.83 (s, 1H), 3.91 (brs, 1H), 3.44 (brs, 1H), 2.12 (s, 3H), 1.99 (s, 3H), 1.23 (brs, 6H), 1.12 (brs, 6H); MS (M+1) 406.3.

Example 5

N,N-Diethyl-4-[[4-(4-formyl-phenyl)-3,5-dimethyl-pyrazol-1-yl]-(3-methoxy-phenyl)-methyl]-benzamide To a stirring solution of N,N-Diethyl-4-[(4-iodo-3,5-dimethyl-pyrazol-1-yl)-(3-methoxy-phenyl)-methyl]-benzamide (300 mg, 0.58 mmol) in 40 mL EtOH/H$_2$O (9:1) at room temperature was added 4-carboxybenzeneboronic acid (261 mg, 1.74 mmol), sodium carbonate (184 mg, 1.74 mmol) and tetrakistriphenylphosphine palladium (0) (200 mg, 0.174 mmol). The mixture was cooled to −78° C., de-oxygenated under reduced pressure and purged with nitrogen gas. The mixture was refluxed for 3 h, cooled to room temperature, filtered through a Celite pad and concentrated under reduce pressure. Purification of the crude material was accomplished by flash chromatography on a 2×15 cm column, eluting with 50% ethyl acetate/hexanes, collecting 8 mL fractions. The product containing fractions were collected and concentrated to give the desired product (267 mg, 93%) as a clear colorless solid. 300 MHz $^1$H NMR (CDCl$_3$) δ 10.1 (s, 1H), 7.90 (d, J=8.3 Hz, 2H), 7.21–7.42 (m, 7H), 6.78–6.86 (m, 3H), 6.57 (s, 1H), 3.75 (s, 3H), 3.52 (brs, 2H), 3.27 (brs, 2H), 2.26 (s, 6H), 1.24 (brs, 3H), 1.22 (brs, 3H); MS (M+1) 496.2.

The following compound was made using the procedure of Example 5.

N,N-Diethyl-4-[[4-(2-formyl-phenyl)-3,5-dimethyl-pyrazol-1-yl]-(3-methoxy-phenyl)-methyl]-benzamide 300 MHz $^1$H NMR (CDCl$_3$) δ 9.85–9.87 (m, 1H), 7.97–7.99 (m, 1H), 7.59–7.65 (m, 2H), 7.17–7.45 (m, 6H), 6.72–6.85 (m, 3H), 6.57 (s, 1H), 3.74 (s, 3H), 3.51 (brs, 2H), 3.27 (brs, 2H), 2.10 (s, 3H), 2.07 (s, 3H), 1.23 (brs, 3H), 1.15 (brs, 3H); MS (M+1) 496.1.

Example 6

4-[[4-(4-Dibutylaminomethyl-phenyl)-3,5-dimethyl-pyrazol-1-yl]-(3-hydroxy-phenyl)-methyl]-N,N-diethyl-benzamide To a stirring solution of N,N-Diethyl-4-[[4-(4-formyl-phenyl)-3,5-dimethyl-pyrazol-1-yl]-(3-methoxy-phenyl)-methyl]-benzamide (105 mg, 0.21 mmol) in 3 mL CH$_2$Cl$_2$ at room temperature was added di-n-butyl amine (55.0 mg, 0.42 mmol), acetic acid (25.5 mg, 0.42 mmol) and sodium triacetoxyborohydride (90.2 mg, 0.42 mmol). After stirring for 6 hours, the reaction was quenched with NaHCO$_3$, the layers were separated, and the aqueous layer was extracted with CH$_2$Cl$_2$ (3×10 mL). The combined organic layers were dried over MgSO$_4$, filtered and concentrated to yield a yellow oil that was used in the next step without further purification.

The crude material prepared above was taken up in 5 mL of aqueous hydrobromic acid solution and heated to gentle reflux for 4 hours. The reaction was cooled to room temperature, poured slowly into a cold aqueous solution of ammonium hydroxide and diluted with methylene chloride. The layers were separated, the aqueous layer was extracted with methylene chloride and the combined organic layers were dried and concentrated. The resulting crude material was purified by flash chromatography with 75% ethyl acetate/hexanes to give 44 mg, (35% yield over two steps) of the desired phenol. 400 MHz $^1$H NMR (CDCl$_3$) δ 7.03–7.35 (m, 9H), 6.74 (s, 1H), 6.65 (d, J=7.7 Hz, 1H), 6.53–6.56 (m, 2H), 3.54–3.59 (m, 4H), 3.31 (brs, 2H), 2.41–2.48 (m, 4H), 2.26 (s, 3H), 2.19 (s, 3H), 1.41–1.46 (m, 4H), 1.22–1.33 (m, 7H), 1.09 (brs, 3H), 0.83–0.88 (m, 6H); MS (M+1) 595.3.

The following compounds were made using the procedure of Example 6.

4-[[4-(2-Dibutylaminomethyl-phenyl)-3,5-dimethyl-pyrazol-1-yl]-(3-hydroxy-phenyl)-methyl]-N,N-diethyl-benzamide 400 MHz $^1$H NMR (CDCl$_3$) δ 7.01–7.65 (m, 9H), 6.51–6.94 (m, 4H), 3.51 (brs, 2H), 3.24–3.28 (m, 4H), 2.01–2.23 (m, 4H), 1.98 (s, 3H), 1.97 (s, 3H), 1.08–1.23 (m, 14H), 0.77–0.86 (m, 6H); MS (M+1) 595.2.

4-[[3,5-Dimethyl-4-(4-piperidin-1-ylmethyl-phenyl)-pyrazol-1-yl]-(3-hydroxy-phenyl)-methyl]-N,N-diethyl-benzamide 400 MHz $^1$H NMR (CDCl$_3$) δ 7.30 (d, J=8.3 Hz, 2H), 7.08–7.23 (m, 5H), 7.03 (d, J=7.9 Hz, 2H), 6.72 (s, 1H), 6.65 (d, J=7.7 Hz, 1H), 6.53–6.55 (m, 2H), 3.48–3.53 (m, 4H), 3.32 (brs, 2H), 2.42 (brs, 4H), 2.18 (s, 3H), 1.98 (s, 3H), 1.56–1.61 (m, 4H), 1.43 (brs, 2H), 1.25 (brs, 3H), 1.09 (brs, 3H); MS (M+1) 551.1.

4-[[3,5-Dimethyl-4-(2-piperidin-1-ylmethyl-phenyl)-pyrazol-1-yl]-(3-hydroxy-phenyl)-methyl]-N,N-diethyl-benzamide MS (M+1) 551.1

4-[[4-(2-Diethylaminomethyl-phenyl)-3,5-dimethyl-pyrazol-1-yl]-(3-hydroxy-phenyl)-methyl]-N,N-diethyl-benzamide MS (M+1) 539.3

4-[[4-(2-Azetidin-1-ylmethyl-phenyl)-3,5-dimethyl-pyrazol-1-yl]-(3-hydroxy-phenyl)-methyl]-N,N-diethyl-benzamide MS (M+1) 523.3

4-[[4-(2-Dimethylaminomethyl-phenyl)-3,5-dimethyl-pyrazol-1-yl]-(3-hydroxy-phenyl)-methyl]-N,N-diethyl-benzamide MS (M+1) 511.3

4-[{3,5-Dimethyl-4-[2-(4-methyl-piperazin-1-ylmethyl)-phenyl]-pyrazol-1-yl}-(3-hydroxy-phenyl)-methyl]-N,N-diethyl-benzamide MS (M+1) 566.3

4-[{4-[2-(Benzylamino-methyl)-phenyl]-3,5-dimethyl-pyrazol-1-yl}-(3-hydroxy-phenyl)-methyl]-N,N-diethyl-benzamide MS (M+1) 573.3

4-[(3,5-Dimethyl-4-{2-[(1-phenyl-ethylamino)-methyl]-phenyl}-pyrazol-1-yl)-(3-hydroxy-phenyl)-methyl]-N,N-diethyl-benzamide MS (M+1) 587.3

4-[{4-[2-(tert-Butylamino-methyl)-phenyl]-3,5-dimethyl-pyrazol-1-yl}-(3-hydroxy-phenyl)-methyl]-N,N-diethyl-benzamide MS (M+1) 539.3

4-[[3,5-Dimethyl-4-(2-thiomorpholin-4-ylmethyl-phenyl)-pyrazol-1-yl]-(3-hydroxy-phenyl)-methyl]-N,N-diethyl-benzamide MS (M+1) 569.3

4-[[3,5-Dimethyl-4-(2-morpholin-4-ylmethyl-phenyl)-pyrazol-1-yl]-(3-hydroxy-phenyl)-methyl]-N,N-diethyl-benzamide MS (M+1) 553.1

4-[{3,5-Dimethyl-4-[2-(3,4,4a,8a-tetrahydro-2H-quinolin-1-ylmethyl)-phenyl]-pyrazol-1-yl}-(3-hydroxy-phenyl)-methyl]-N,N-diethyl-benzamide MS (M+1) 599.3

4-[{3,5-Dimethyl-4-[2-(3,4,4a,8a-tetrahydro-1H-isoquinolin-2-ylmethyl)-phenyl]-pyrazol-1-yl}-(3-hydroxy-phenyl)-methyl]-N,N-diethyl-benzamide MS (M+1) 599.3

What is claimed is:

1. A compound of the formula (I):

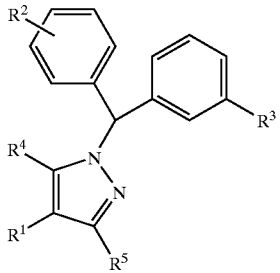

I and pharmaceutically acceptable salts thereof;

wherein $R^1$ is an aryl selected, from phenyl and naphthyl, wherein any of the above aryl moieties of $R^1$ may optionally be substituted with from one to three substituents independently selected from halogen, $(C_1–C_6)$ alkyl optionally substituted with from one to seven fluorine atoms, phenyl, benzyl, hydroxy, acetyl, formyl, amino, cyano, nitro, $(C_1–C_6)$alkoxy, $(C_1–C_6)$ alkylamino, $[(C_1–C_6)alkyl]_2$amino, benzylamino $(C_1–C_8)$alkyl,$(C_1–C_8)$alkylamino$(C_1–C_8)$alkyl, $(R^6)_2$ amino$(C_1–C_8)$alkyl wherein each $R^6$ is $(C_1–C_6)$alkyl or two $R^6$ groups join to form a saturated 4 to 6-membered ring optionally containing one heteroatom selected from O, N or S, said 4 to 6-membered ring optionally substituted by a $(C_1–C_6)$alkyl or a benzo group at any two adjacent carbon atoms, and wherein any of alkyl moieties in $R^1$ may optionally be substituted with from one to seven fluorine atoms;

$R_2$ is halogen, aryl, heteroaryl, $SO_2R^7$, $COR^7$, $CONR^8R^9$, $COOR^7$, or $C(OH)R^8R^9$ wherein each of $R^7$, $R^8$ and $R^9$ is defined, independently, as $R^1$ is defined above, or $R^7$ and $R^8$, together with the carbon or nitrogen to which they are both attached, form a three to seven membered saturated ring containing from zero to three heteroatoms selected, independently, from O, N and S, and wherein said aryl and heteroaryl are defined as such terms are defined above in the definition of $R^1$, and wherein any of the aryl, heteroaryl and heterocyclic moieties of $R^2$ may optionally be substituted with from one to three substituents independently selected from halo, $(C_1–C_6)$alkyl optionally substituted with from one to seven fluorine atoms, phenyl, benzyl, hydroxy, acetyl, amino, cyano, nitro, $(C_1–C_6)$alkoxy optionally substituted with from one to seven fluorine atoms, $(C_1–C_6)$alkylamino and $[(C_1–C_6)alkyl]_2$amino;

$R^3$ is hydroxy, —$(C_1–C_6)$alkyl-OH, $(C_1–C_6)$alkoxy, —$(C_1–C_7)$alkyl-$(C_1–C_7)$alkoxy, $NHSO_2R^7$, $C(OH)R^7R^8$, fluorine, bromine, chlorine, iodine, triazolyl, tetrazolyl, heteroaryl, as defined for $R^1$ above or $CONHR^7$, wherein $R^7$ and $R^8$ are the same or different and are selected from hydrogen, $(C_1–C_4)$alkyl, $(C_1–C_4)$ alkoxy and $(C_1–C_4)$alkoxy-$(C_1–C_4)$alky-1 having a total of 4 or less carbon atoms, and wherein any of the alkyl moieties of $R^7$ and $R^8$ may optionally be substituted with from one to seven fluorine atoms; and $R^4$ and $R^5$ are each, independently, $(C_1–C_8)$alkyl, $(C_3–C_7)$ cycloalkyl-, or $(C_3–C_7)$cycloalkyl-$(C_1–C_8)$alkyl.

2. A compound according to claim 1 wherein $R^1$ is wherein the aryl in $R^1$ may optionally be substituted with from one to three substituents independently selected from halogen, $(C_1–C_6)$alkyl optionally substituted with from one to seven fluorine atoms, phenyl, benzyl, hydroxy, acetyl, formyl, amino, cyano, nitro, $(C_1–C_6)$ alkoxy, $(C_1–C_6)$alkylamino, $[(C_1–C_6)alkyl]_2$amino, benzylamino$(C_1–C_8)$alkyl, $(C_1–C_8)$alkylamino$(C_1–C_8)$ alkyl, $(R^6)_2$amino$(C_1–C_8)$alkyl wherein each $R^6$ is $(C_1–C_6)$alkyl or two $R^6$ groups join to form a saturated 4 to 6-membered ring optionally containing one heteroatom selected from O, N or S, said 4 to 6-membered ring optionally substituted by a $(C_1–C_6)$alkyl or a benzo group at any two adjacent carbon atoms, and wherein any of alkyl moieties in $R^1$ may optionally be substituted with from one to seven fluorine atoms;

$R^2$ is aryl, halo, heteroaryl, $SO_2R^7$, $COR^7$, $CONR^5R^9$, $COOR^7$, or $C(OH)R^8R^9$ wherein each of $R^7$, $R^8$ and $R^9$ is defined, independently, as $R^1$ is defined above, or $R^7$ and $R^8$, together with the carbon or nitrogen to which they are both attached, form a three to seven membered saturated ring containing from zero to three heteroatoms selected, independently, from O, N and S, and wherein said aryl and heteroaryl are defined as such terms are defined above in the definition of $R^1$, and wherein any of the aryl, heteroaryl and heterocyclic moieties of $R^2$ may optionally be substituted with from one to three substituents independently selected from halo, $(C_1-C_6)$alkyl optionally substituted with from one to seven fluorine atoms, phenyl, benzyl, hydroxy, acetyl, amino, cyano, nitro, $(C_1-C_6)$alkoxy optionally substituted with from one to seven fluorine atoms, $(C_1-C_6)$alkylamino and $[(C_1-C_6)$alkyl$]_2$amino;

$R^3$ is hydroxy, —$(C_1-C_6)$alkyl-OH, $(C_1-C_6)$alkoxy, —$(C_1-C_6)$alkyl-$(C_1-C_6)$alkoxy-, $NHSO_2R^7$, C(OH) $R^7$, $R^8$, fluorine, bromine, chlorine, iodine, triazolyl, tetrazolyl, heteroaryl, as defined for $R^1$ above or $CONHR^7$, wherein $R^7$ and $R^8$ are the same or different and are selected from hydrogen, $(C_1-C_4)$alkyl, $(C_1-C_4)$alkoxy and $(C_1-C_4)$alkoxy-$(C_1-C_4)$alky-1 having a total of 4 or less carbon atoms, and wherein any of the alkyl moieties of $R^7$ and $R^1$ may optionally be substituted with from one to seven fluorine atoms; and $R^4$ and $R^5$ are each, independently, $(C_3-C_7)$cycloalkyl- or $(C_3-C_7)$cycloalkyl-$(C_1-C_8)$alkyl.

3. A compound according to claim 1 wherein $R^1$ is naphthyl or phenyl, wherein the above phenyl or naphthyl may optionally be substituted with one or two substituents, independently selected from halogen, hydroxy, $(C_1-C_6)$alkyl optionally substituted with from one to seven fluorine atoms, formyl, $(C_1-C_8)$alkylamino$(C_1-C_8)$alkyl, and $(R^6)_2$amino$(C_1-C_8)$alkyl wherein each $R^6$ is $(C_1-C_6)$alkyl or two $R^6$ groups join to form a saturated 4 to 6-membered ring optionally containing one heteroatom selected from O, N or S, said 4 to 6-membered ring optionally substituted by a $(C_1-C_6)$alkyl or a benzo group at any two adjacent carbon atoms; and $R_2$ is $CONR^8R^9$ or $COOR^7$, wherein each of $R^7$, $R^8$ and $R^9$ is $(C_1-C_6)$alkyl optionally substituted with from one to seven fluorine atoms;

$R^3$ is hydroxy, $(C_1-C_8)$alkoxy, or halogen; and $R^1$ and $R^5$ are each $(C_1-C_8)$alkyl.

4. A compound according to claim 1 wherein $R^1$ is naphthyl or phenyl optionally substituted with one or more halogen, hydroxy, trifluoromethyl, alkyl, formyl, $(C_1-C_6)$alkylaminomethy-1, $((C_1-C_6))_2$ aminomethyl, piperidinylmethyl, azetidinylmethyl, $(C_1-C_6)$alkylpipiridinylmethyl, benzylaminomethyl, morpholinylmethyl, thiomorpholinylmethyl, isoquinolinylmethyl, or quinolinylmethyl;

$R^2$ is $(C_1-C_6)$alkylaminocarbonyl, $((C_1-C_6))_2$ aminocarbonyl or alkoxycarbonyl;

$R^3$ is hydroxy or $(C_1-C_6)$alkoxy; and $R^4$ and $R^5$ each $(C_1-C_6)$alkyl.

5. A compound selected from the group consisting of:

N,N-Diethyl-4-[[4-(4-fluoro-phenyl)-3,5-dimethyl-pyrazol-1-yl]-(3-hydroxy-phenyl)-methyl]-benzamide;

4-[(3,5-Dimethyl-4-phenyl-pyrazol-1-yl)-(3-hydroxy-phenyl)-methyl]-N,N-diethyl-benzamide;

4-[[4-(4-Chloro-phenyl)-3,5-dimethyl-pyrazol-1-yl](3-hydroxy-phenyl)-methyl]-N,N-diethyl-benzamide;

4-[(3,5-Dimethyl-4-p-tolyl-pyrazol-1-yl)-(3-hydroxy-phenyl)-methyl]-N,N-diethyl-benzamide;

4-[[3,5-Dimethyl-4-(4-trifluoromethyl-phenyl)-pyrazol-1-yl]-(3-hydroxy-phenyl)-methyl]-N,N-diethyl-benzamide;

4-[(3,5-Dimethyl-4-m-tolyl-pyrazol-1-yl)-(3-hydroxy-phenyl)-methyl]-N,N-diethyl-benzamide;

4-[(3,5-Dimethyl-4-o-tolyl-pyrazol-1-yl)-(3-hydroxy-phenyl)-methyl]-N,N-diethyl-benzamide;

4-[[4-(3,5-Dichloro-phenyl)-3,5-dimethyl-pyrazol-1-yl]-(3-hydroxy-phenyl)-methyl]-N,N-diethyl-benzamide;

4-[[4-(2,4-Dichloro-phenyl)-3,5-dimethyl-pyrazol-1-yl]-(3-hydroxy-phenyl)-methyl]-N,N-diethyl-benzamide;

4-[[3,5-Dimethyl-4-(2-piperidin-1-ylmethyl-phenyl)-pyrazol-1-yl]-(3-hydroxy-phenyl)-methyl]-N,N-diethyl-benzamide;

4-[[4-(2-Diethylaminomethyl-phenyl)-3,5-dimethyl-pyrazol-1-yl]-(3-hydroxy-phenyl)-methyl]-N,N-diethyl-benzamide;

4-[[4-(2-Azetidin-1-ylmethyl-pheny-1)--3,5dimethyl-pyrazol-1-yl]-(3-hydroxy-phenyl)-methyl]-N,N-diethyl-benzamide;

4-[[3,5-Dimethyl-4-(2-morpholin-4-ylmethyl-phenyl)-pyrazol-1yl]-(3-hydroxy-phenyl)-methyl]-N,N-diethyl-benzamide;

and pharmaceutically acceptable salts thereof.

6. A pharmaceutical composition comprising a compound according to claim 1 or a pharmaceutically acceptable salt thereof, and a pharmaceutically acceptable carrier.

* * * * *